US007426037B2

(12) United States Patent
Ostrovsky et al.

(10) Patent No.: US 7,426,037 B2
(45) Date of Patent: Sep. 16, 2008

(54) DIFFRACTION GRATING BASED INTERFEROMETRIC SYSTEMS AND METHODS

(75) Inventors: Isaac Ostrovsky, Wellesley, MA (US); Mark D. Modell, Natick, MA (US); Robert J. Crowley, Sudbury, MA (US)

(73) Assignee: Boston Scientific Scimed, Inc., Valencia, CA (US)

( * ) Notice: Subject to any disclaimer, the term of this patent is extended or adjusted under 35 U.S.C. 154(b) by 0 days.

(21) Appl. No.: 11/531,211

(22) Filed: Sep. 12, 2006

(65) Prior Publication Data

US 2007/0024869 A1     Feb. 1, 2007

Related U.S. Application Data

(63) Continuation of application No. 11/166,522, filed on Jun. 24, 2005, now Pat. No. 7,130,054, which is a continuation of application No. 10/017,534, filed on Oct. 18, 2001, now Pat. No. 7,006,231.

(51) Int. Cl.
*G01B 11/02* (2006.01)
*G01B 9/02* (2006.01)

(52) U.S. Cl. ...................... 356/479; 356/521

(58) Field of Classification Search ............ 356/479, 356/497, 521
See application file for complete search history.

(56) References Cited

U.S. PATENT DOCUMENTS 5,321,501 A    6/1994   Swanson et al.

(Continued)

FOREIGN PATENT DOCUMENTS

WO     WO 98/38907     9/1998

OTHER PUBLICATIONS

I. Zeylikovich et al., Nonmechanical Grating-Generated Scanning Coherence Microscopy, Dec. 1, 1998 (Received Jun. 22, 1998), vol. 23 No. 23 Optics Letters, Optical Society of America.

*Primary Examiner*—Patrick J Connolly
(74) *Attorney, Agent, or Firm*—Darby & Darby PC; Bruce E. Black

(57) ABSTRACT

Diffraction grating based fiber optic interferometric systems for use in optical coherence tomography, wherein sample and reference light beams are formed by a first beam splitter and the sample light beam received from a sample and a reference light beam are combined on a second beam splitter. In one embodiment, the first beam splitter is an approximately 50/50 beam splitter, and the second beam splitter is a non 50/50 beam splitter. More than half of the energy of the sample light beam is directed into the combined beam and less than half of the energy of the reference light beam are directed into the combined beam by the second beam splitter. In another embodiment, the first beam splitter is a non 50/50 beam splitter and the second beam splitter is an approximately 50/50 beam splitter. An optical circulator is provided to enable the sample light beam to bypass the first beam splitter after interaction with a sample. Two combined beams are formed by the second beam splitter for detection by two respective detectors. More than half of the energy of the light source provided to the first beam splitter is directed into the sample light beam and less than half of the energy is directed into the reference light beam. The energy distribution between the sample and reference light beams can be controlled by selection of the characteristics of the beam splitters.

24 Claims, 14 Drawing Sheets

U.S. PATENT DOCUMENTS

| | | |
|---|---|---|
| 5,383,467 A | 1/1995 | Auer et al. |
| 5,459,570 A | 10/1995 | Swanson et al. |
| 5,619,325 A | 4/1997 | Yoshida |
| 5,715,825 A | 2/1998 | Crowley |
| 5,883,717 A | 3/1999 | DiMarzio et al. |
| 5,943,133 A | 8/1999 | Zeylikovich et al. |
| 6,002,480 A | 12/1999 | Izatt et al. |
| 6,111,645 A | 8/2000 | Tearney et al. |
| 6,134,003 A | 10/2000 | Tearney et al. |
| 6,256,102 B1 | 7/2001 | Dogariu |
| 6,728,571 B1 | 4/2004 | Barbato |
| 6,847,454 B2 * | 1/2005 | Crowley et al. ............. 356/479 |
| 7,006,231 B2 * | 2/2006 | Ostrovsky et al. ........... 356/479 |
| 7,130,054 B2 * | 10/2006 | Ostrovsky et al. ........... 356/479 |
| 2003/0137670 A1 | 7/2003 | Barbato |
| 2006/0055936 A1 | 3/2006 | Yun et al. |

* cited by examiner

DIFFRACTION GRATING BASED INTERFEROMETRIC SYSTEMS AND METHODS

RELATED APPLICATIONS

The present application is a continuation of U.S. application Ser. No. 11/166,522, filed Jun. 24, 2005, now U.S. Pat. No. 7,130,054 which is a continuation of U.S. patent application Ser. No. 10/017,534, filed Oct. 18, 2001, now U.S. Pat. No. 7,006,231, which is related to U.S. patent application Ser. No. 10/020,040, filed, Oct. 18, 2001, now U.S. Pat. No. 6,847,454, all of which are incorporated by reference herein.

FIELD OF THE INVENTION

This invention relates generally to diffraction grating based interferometers and, more particularly, to diffraction grating based interferometric systems for use in optical coherence tomography.

BACKGROUND OF THE INVENTION

Optical Coherence Tomography ("OCT") is a type of optical coherence-domain reflectometry that uses low coherence interferometry to perform high resolution ranging and cross-sectional imaging. In OCT systems, a light beam from a low coherence light source is split into a reference light beam and a sample light beam. A diffraction grating may be used to provide an optical path difference in one or both light beams. The sample light beam is directed onto a sample and the light scattered from the sample is combined with the reference light beam. The combination of the sample and reference light beams results in an interference pattern corresponding to the variation in the sample reflection with the depth of the sample, along the sample beam. The sample beam typically suffers a high loss of energy due to its interaction with the sample. The reference beam serves as a local oscillator to amplify the interference pattern to a detectable level and therefore must have a much higher energy level than the sample light beam. The interference pattern is detected by a photo detector, whose output is processed to generate a cross-sectional image of the sample. High resolution (less than 10 micrometer) imaging of the cross-sections of the sample by OCT is useful in biological and medical examinations and procedures, as well as in materials and manufacturing applications.

OCT based systems may be implemented with fiber optics and an optical fiber carrying the sample light beam may be incorporated into a catheter or an endoscope for insertion into internal body cavities and organs, such as blood vessels, the gastrointestinal tract, the gynecological tract and the bladder, to generate images of internal cross-sections of the cavities or organs. The sample beam is typically emitted from the distal end of the instrument, where a prism or a mirror, for example, directs the sample light beam towards a wall of the cavity. The optical fiber and the prism or mirror may be rotated by a motor to facilitate examination of the circumference of the cavity.

An example of a fiber optic OCT system is shown in U.S. Pat. No. 5,943,133 ("the '133 patent"), where sample and reference light beams are carried in respective optical fibers to a diffraction grating, which introduces an optical path difference across the light beams and also combines the sample and reference light beams. FIG. 1 is a schematic diagram of a system 10 disclosed in the '133 patent. The system includes a light source 12 optically coupled to a 50/50 beam splitter 14 through an optical fiber 16. The beam splitter 14 splits the incident light beam equally into a sample light beam and a reference light beam. The sample light beam is carried by an optical fiber 18 to a focusing lens 20, which focuses the sample light beam onto a sample 22. The optical fiber 18 may be contained within a catheter (not shown) for insertion into a body cavity, such as a blood vessel, for examination of the tissue of the wall of the cavity. Light received from the tissue is focused by the lens 20 and coupled back into the optical fiber. The received light travels back to the beam splitter 14, where it is split again. A portion of the received light is directed into another optical fiber 24, which conveys the light to a first collimator 26. The reference light beam travels through an optical fiber 28 to a second collimator 30. The first and second collimators 26, 30 direct the sample and reference light beams onto the same region of a diffraction grating 32. The diffracted, combined light beam is conjugated on the detector plane of a multi-channel linear diode array detector 34 by a conjugating 36 lens. A neutral density filter (not shown) is provided to decrease the energy in the reference beam to prevent saturation of the detector.

The sample light beam suffers a significant loss of energy due to its interaction with the sample. The second pass through the 50/50 beam splitter further reduces the already attenuated light beam. In addition, the interaction of the light beams with the diffraction grating causes a further loss in both the sample light beam and the reference light beam of about 50% of the incident light in the first order. The diffraction grating also introduces noise. As a result, the system of the '133 patent has a low signal-to-noise ratio.

Another interferometric system using a diffraction grating is described in "Nonmechanical grating-generated scanning coherence microscopy", Optics Letters, Vol. 23, No. 23, Dec. 1, 1998. FIG. 2 is a schematic diagram of the disclosed system 50. A light source 52 provides light to a 50/50 beam splitter 54 that splits the energy in the light beam equally into a sample light beam 55 and a reference light beam 56. The sample light beam 55 is directed to a focusing lens 58 that focuses the sample light beam onto a sample 60. The light received by the focusing lens 58 from the sample 60 is returned to the beam splitter 54. The reference light beam 56 is directed to a diffraction grating 62 in a Littrow configuration, which introduces an optical path difference across the reference light beam. The diffracted reference light beam is also returned to the beam splitter 54. The sample and reference light beams are then combined in the beam splitter 54 and directed to a charge-coupled device (CCD) array 64 for detection and processing by a computer 66. The reference light beam needs to be suppressed here, as well.

Here, only the reference light beam is diffracted, making the system 50 more efficient than the system 10 of the '133 patent, shown in FIG. 1. However, the sample and reference arms in the system 50 of FIG. 2 cannot both be implemented with fiber optics. The diffraction grating introduces an optical path difference across the width of the beam. The detector is a multi-element detector at least as wide as the light beam and each element of the detector receives a portion of the beam corresponding to its position on the diffraction grating. If the reference light beam is conveyed by an optical fiber from the diffraction grating to the detector, the spatial order is lost. If the sample arm is implemented in fiber optics but the reference arm is not, the length of the open space reference arm would be inconveniently long.

In OCT systems, either the reference light beam or the sample light beam may be modulated to provide a relatively low frequency beating used as a carrier frequency. The mechanical motion may be used to scan the optical path, which essentially represents the sample depth. This motion also creates a Doppler frequency shift. A moving or oscillating mirror and a fiber stretcher, such as a piezoelectric stretcher, are commonly used for mechanically modulating the light. One or a pair of acousto-optic modulators may also be used to modulate the light beam, as described in U.S. Pat. No. 5,321,501, for example. The amplitude of the frequency of modulation is modulated by the intensity of the reflected and scattered light in the sample beam. The signal is then processed using a narrow band amplifier tuned to the frequency, to extract the intensity variation to produce an image.

In diffraction grating based interferometry using a multi-element photo detector, scanning the depth is typically not necessary because the depth is instantly projected onto the multi-element photo detector. Depending on the signal processing method, however, there may be a need for low frequency modulation. For example, if the detector is a photo diode array and heterodyne signal processing is used, low frequency modulation is required. Providing a separate modulating unit in the interferometer takes up additional space and adds to the complexity of the system. If the detector is a charge coupled device (CCD), modulation is not needed.

In prior art diffraction grating based OCT systems, the sample light beam typically passes through the beam splitter that creates the sample and the reference light beams, twice. It is therefore most efficient to use a 50/50 beam splitter that directs half of the energy from the light source into the reference beam and half of the energy into the sample beam. However, much of the energy in the reference light beam needs to be suppressed to prevent saturation of the detector. Such energy is lost in the system. The sample light beam, which suffers high loss due to its interaction with the sample as well as the second pass through the beam splitter, only receives half of the energy of the light source. The sample light beam also suffers loss and noise if it is diffracted by the diffraction grating. A more efficient diffraction grating based interferometer for use in OCT systems would be advantageous. A more efficient diffraction based interferometer, where the sample and reference light beams are carried by optical fibers, would also be advantageous.

SUMMARY OF THE INVENTION

In one embodiment of the invention, an interferometer is disclosed comprising a low coherence light source and a first beam splitter in communication with the light source to split light from the light source into a first sample light beam to be directed onto a sample and a reference light beam. Light received from the sample forms a second sample light beam. A diffraction grating is positioned to diffract at least one of the reference light beam or the second sample light beam. The diffraction grating introduces an optical path difference across the diffracted light beam. A second beam splitter is positioned to receive the second sample light beam and the reference light beam, after at least one of those beams has been diffracted. The second sample light beam and the reference light beam are combined in the second beam splitter to form a combined light beam. A detector is positioned to receive the combined light beam from the second beam splitter. Preferably, the detector is a multi-element detector. A signal processor, such as a computer, processes the output from the detector into an image for display.

Preferably, the reference light beam is diffracted and the sample light beam is directed onto the second beam splitter without being diffracted. By only diffracting the reference light beam and combining the sample light beam with the diffracted reference light beam on a second beam splitter, the sample light beam does not suffer from loss and noise due to interacting with the diffraction grating.

In one variation of this embodiment, the second beam splitter is a non 50/50 beam splitter. The first beam splitter may be an approximately 50/50 beam splitter and the characteristics of the second beam splitter may be adjusted so that a sufficient amount of energy is provided by the reference beam to amplify the sample beam for analysis, without saturating the detector. For example, the second beam splitter may direct more than half of the light energy of the second sample light beam into the combined beam and less than half of the light energy of the reference light beam into the combined beam. Preferably, the second beam splitter directs substantially more than half of the light energy of the second sample light beam and substantially less than half of the light energy of the reference light beam into the combined beam. More preferably, the second beam splitter directs at least about 90% of the light energy of the second sample light beam into the combined light beam and directs about 10% or less of the light energy of the reference light beam into the combined light beam.

In another variation of this embodiment, the first beam splitter is a non 50/50 beam splitter. The first beam splitter directs more than half of the light energy received from the light source into the sample light beam and less than half of the light energy received from the light source into the reference light beam. An optical circulator may be provided to direct the sample light beam to the sample and to direct the second sample light beam from the sample to the second beam splitter. Use of an optical circulator enables the light received from the sample under examination to bypass the first beam splitter. The first beam splitter need not, therefore, be a 50/50 beam splitter, and its characteristics may be adjusted to optimize the energy distribution between the sample and reference light beams. For example, substantially more than half of the light energy received from the light source is preferably directed into the sample light beam and substantially less than half of the light energy received from the light source is directed into the reference light beam. More preferably, at least about 90% of the light energy received from the light source is directed into the sample light beam and about 10% or less of the light energy received from the light source into the reference light beam.

The second beam splitter may be an approximately 50/50 beam splitter and the second sample light beam and the reference beam may be combined in the second beam splitter to form first and second combined light beams. In that case, the first light beam may be detected by the first detector and a second detector may be provided to detect the second light beam.

In another embodiment of the invention, first and second low coherence light sources are provided in an interferometer, each emitting light at a different wavelength. A first beam splitter receives the light from the light sources and forms sample and reference light beams. The sample light beam is directed onto a sample and light received from the sample forms a second sample light beam. At least one of the reference light beam or the second sample light beam is diffracted. A second beam splitter forms two combined light beams from the reference light beam and the second sample light beam and two detectors are provided, one to detect each beam.

In another embodiment of the invention, an interferometer comprises a beam splitter that forms two combined light beams for detection by two detectors. Polarization filters having different polarizations are provided between the beam splitter and each detector. Birefrigence measurements may thereby be made.

In another embodiment of the invention, a fiber optic interferometer is disclosed wherein the sample and reference light beams are combined on a beam splitter. A first fiber optic beam splitter splits the light received from a light source along an optical fiber into a sample light beam and a reference light beam. The sample light beam is conveyed from the beam splitter to a sample by another optical fiber. The light received from the sample is coupled back into the optical fiber, and returned to the fiber optic beam splitter. The light received from the sample is conveyed from the fiber optic beam splitter to a second beam splitter by another optical fiber. Meanwhile, the reference light beam is conveyed from the fiber optic beam splitter to a diffraction grating by another optical fiber. The diffraction grating introduces an optical path difference across the reference light beam. The diffraction grating directs a diffracted reference light beam to the second beam splitter, where it combines with the second sample light beam. The combined light beam is directed toward a detector for detection. Preferably, the detector is a multi-element photo detector. A signal processor processes the output of the detector into an image for display on a monitor, for example.

By providing two beam splitters, one to form the sample and reference light beams and the other to combine the sample and reference light beams, the sample light beam may be carried by optical fibers to the sample to be analyzed and to the second beam splitter while the reference light beam may be carried by an optical fiber to the diffraction grating. A fiber optic OCT system may thereby be implemented.

Preferably, the first beam splitter is an approximately 50/50 beam splitter and the second beam splitter is a non 50/50 beam splitter. The second, non 50/50 beam splitter directs more than half, and preferably substantially more than half, of the energy of the sample light beam and less than half, and preferably substantially less than half, of the energy of the diffracted reference light beam into the combined beam. More preferably, at least about 90% of the light energy is directed into the sample light beam and about 10% or less of the light energy is directed into the reference light beam.

In another embodiment of the invention implemented with fiber optics, the first beam splitter, that splits the light from the light source into a sample and reference beam, is a non 50/50 beam splitter. More than half, and preferably substantially more than half, of the light energy of the light received from the source is directed into the sample light beam and less than half, and preferably substantially less than half, of the light energy is directed into the reference light beam. More preferably, at least about 90% of the light energy is directed into the sample light beam and about 10% or less of the light energy is directed into the reference light beam. The sample light beam is provided from the first beam splitter to an optical circulator by an optical fiber. Another optical fiber conveys the sample light beam to the sample to be analyzed. Light received from the sample is conveyed back to the optical circulator by the same optical fiber. The received light is then conveyed from the optical circulator to a second beam splitter. Meanwhile, the reference light beam is conveyed by an optical fiber to a diffraction grating. The diffraction grating reflects the diffracted reference light beam onto the second beam splitter, for combination with the sample light beam.

The second beam splitter may be a 50/50 beam splitter. Two combined light beams with the same proportion of energy from the sample and reference light beams are thereby formed, which may be detected by two detectors. Preferably, the detector detectors are each multi-element photo detectors. A signal processor processes the output of the detector or detectors into an image for display.

Alternatively, the second beam splitter may also be a non 50/50 beam splitter that directs more than half of the energy of the sample light beam and less than half of the energy of the diffracted reference light beam into a combined beam directed toward a single detector, which is also preferably a multi-element photo detector. The characteristics of the second beam splitter may also be adjusted so that a sufficient amount of energy is provided by the reference beam to amplify the sample beam for analysis, without saturating the detector.

DETAILED DESCRIPTION OF THE PREFERRED EMBODIMENTS

Figure 3A:
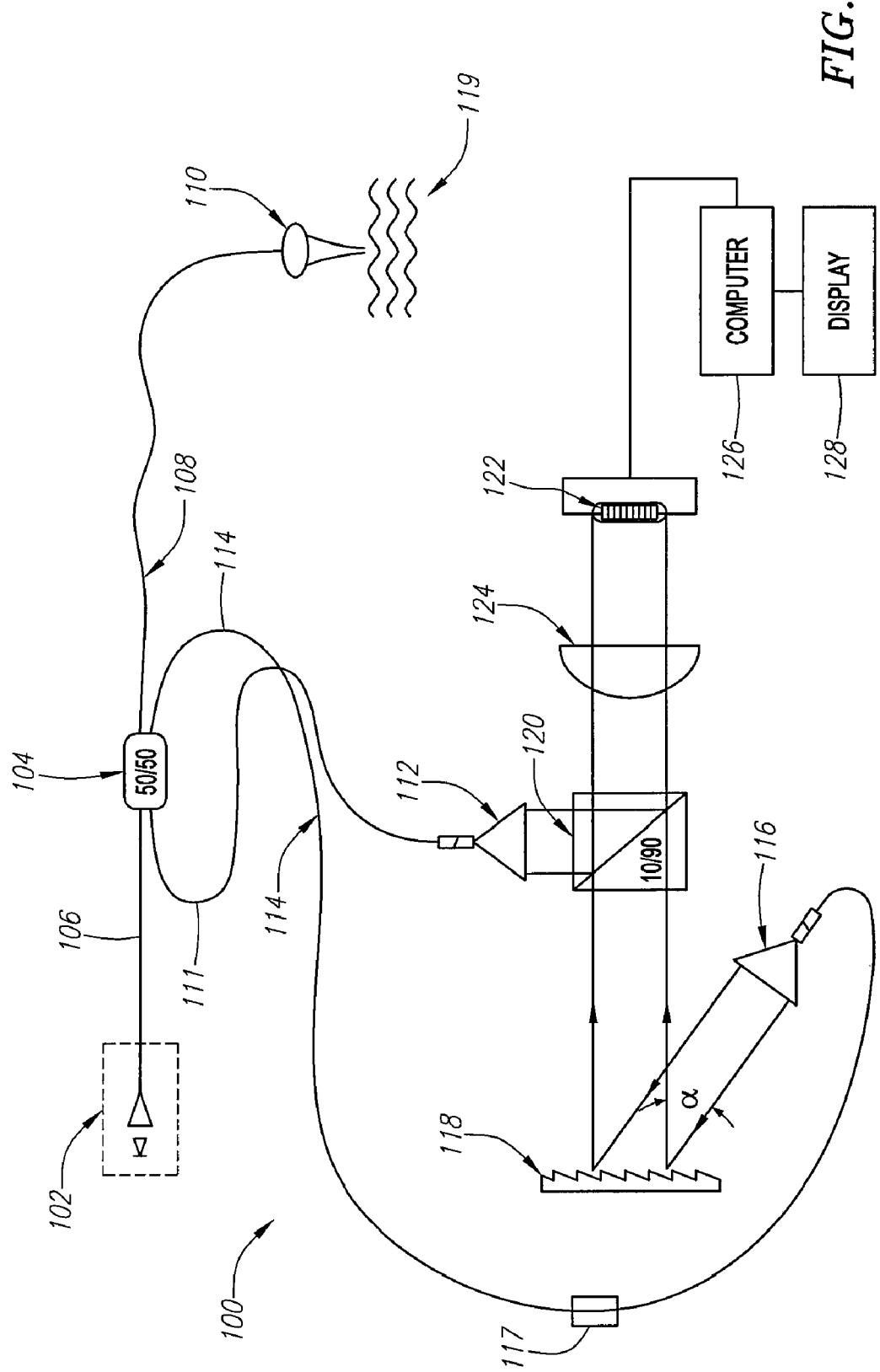
FIG. 3a is a schematic diagram of a diffraction grating based fiber optic interferometric system in accordance with one embodiment of the invention.

FIG. 3a is a schematic diagram of one embodiment of a diffraction grating based fiber optic interferometric system 100. The system 100 comprises a light source 102 optically coupled to a fiber optic beam splitter 104 by an optical fiber 106. The fiber optic beam splitter 104 is preferably approximately a 50/50 beam splitter. More preferably, the beam splitter 104 is a 50/50 beam splitter. An optical fiber 108 is optically coupled to the fiber optic beam splitter and to a focusing lens 110.

An optical fiber 111 is also optically coupled to the fiber optic beam splitter 104 such that light entering the beam splitter from the optical fiber 108 is coupled into the optical fiber 110. The optical fiber 111 is also optically coupled to a first collimator 112. Another optical fiber 114 is optically coupled to the first beam splitter 104 and to a second collimator 116.

The optical fibers 108 and 110 comprise first and second parts of a sample arm, respectively, of the interferometric system 100. The optical fiber 114 comprises a reference arm of the system 100. Light from the light source 102 passes through the fiber optic beam splitter 104 and is split into a sample light beam and a reference light beam, each having half of the energy of the initial light beam provided from the light source 102 to the fiber optic beam splitter 104. The sample light beam is directed into the optical fiber 108 of the first part of the sample arm and the reference light beam is directed into the optical fiber 114 of the reference arm. The sample light beam is focused by the focusing lens 110 onto a sample of interest 119, which may be tissue within a body cavity, for example. Light scattered by the sample is focused by the focusing lens 110 to form a second sample light beam and is coupled back into the optical fiber 108 of the sample arm. That light passes back through the first beam splitter 104, where the light beam is split again. A light beam having half of the energy of the received light beam is coupled into the optical fiber 110 of the second part of the sample arm.

The second collimator 116 collimates the reference light beam and directs the reference light beam onto a diffraction grating 118 at an angle α. The diffraction grating 118 introduces an optical path difference to the reference light beam and reflects the diffracted reference light beam onto a second, open space beam splitter 120. The first collimator 112 also collimates the second sample light beam and directs it onto the second beam splitter 120.

The second beam splitter 120 combines the second sample light beam and the reference light beam and directs a portion of the combined light beam onto a photo detector 122, through a conjugating lens 124. The photo detector 112 is preferably a multi-element photo detector, such as a photo diode array. An array of avalanche mode photo diodes may be used, for example. A charge coupled-device ("CCD") may be used, as well. The conjugating lens 124 projects the image of the combined beam on the plane of the second beam splitter onto the detector plane. The detector 122 is connected to a signal processor, such as a computer 126, which processes the data received from the detectors to create an image on a display 128, such as a monitor. The output of the detector 122 may be converted into a digital signal prior to being input to the computer 126. The image may be printed as well.

In accordance with this first embodiment, the open space beam splitter 120 directs less than half of the light energy in the reference beam and more than half of the energy in the second sample light beam into the combined beam directed toward the detector 122. Preferably, substantially more than half of the energy in the second sample light beam, such as 75% or more, is directed into the combined beam and substantially less than half of the energy in the reference light beam, such as 25% or less, is directed into the combined light beam. More preferably, at least about 90% or more of the energy of the sample light beam and about 10% or less of the energy of the reference light beam are directed into the combined beam. For example, the second beam splitter may be a 10/90, 5/95, 2/98 or 1/99 beam splitter. In the embodiment of FIG. 3a, the reference light beam is transmitted through the second beam splitter 120 while the sample light beam is reflected by the second beam splitter 120. Alternatively, the sample light beam may be transmitted through the second beam splitter 120 and the reference light beam may be reflected by the second beam splitter.

As is known in the art, in order for there to be constructive interference between the sample and reference light beams in this and the other embodiments of the invention, the optical path lengths of the sample light beam (the initial sample light beam and the second light beam) and the reference light beam from the first beam splitter 104 to the second beam splitter 120 need to be equal to within the coherence length of the light source 102. The refractive index of the optical fibers and the open space traversed by the light beams, as well as the refractive index of the sample material, need to be considered in determining appropriate path lengths.

The interference pattern resulting from the combination of the sample and reference light beams contains both depth information and brightness information. The brightness information is provided by the light intensities of the interference pattern. Since the portion of the second sample light beam that is received in the sample arm from a certain depth from the sample interferes with a portion of the diffracted reference beam at a spatial position corresponding to the optical path difference for this position, the depth information is provided by the spatial position within the interference pattern. The photo detectors of the array 122 are arranged so that each photo detector element detects the light intensity of the interference pattern at a certain spatial position within the interference pattern, as is known in the art. Thus, the output of each photo detector element provides image brightness information for a certain image depth. The array 122 outputs the information along parallel channels (not shown), where each channel corresponds to the output of one of the photo detector elements. The outputs of the parallel channels of the photo array 122 are provided to the computer 126 for processing in accordance with known processing techniques to produce an image of the sample depth reflection along the sample light beam for display. Preferably, the multi-element detector 122 is a photo diode array and a heterodyne detection technique is used.

As discussed above, if the detector is a photo diode array and a heterodyne detection method is used, low frequency modulation is required. A modulator 117, such as a fiber stretcher or an acousto-optic modulator, is therefore provided along the optical fiber 114. The modulator 117 may be provided along the optical fibers 108 or 111 to modulate the sample light beam, as well.

Use of two beam splitters enables the reference light beam to be conveyed to the diffraction grating 118 by an optical fiber 114. Since the second sample light beam is not combined with the reference light beam on the diffraction grating in this embodiment, additional loss and noise is not introduced to the second sample light beam. Since the optical path from the diffraction grating 118 to the detector 122 is open space, spatial information in the reference and sample light beams is preserved.

The optical fiber 108 of the first part of the sample arm is preferably incorporated in a catheter adapted to be positioned in a body cavity or organ by standard catheter intervention procedures. For example, the catheter may be inserted into a blood vessel or the heart by guiding the flexible catheter through various blood vessels along a circuitous path, starting, for example, by percutaneous introduction through an introducer sheath disposed in a perforation of the femoral artery. Alternatively, the catheter can be introduced directly into a body cavity or body tissue, such as an organ. The optical fiber may be coupled to a motor for causing rotation of the fiber within the catheter. Catheters and endoscopes for use in the optical imaging of blood vessels and other internal body cavities are known in the art and are described in U.S. Pat. No. 6,134,003, U.S. Pat. No. 5,321,501 and International Publication No. WO 98/38907 published on Sep. 11, 1998, for example, which are incorporated by reference herein. As disclosed in those references, a mirror or prism may be provided to reflect the sample light beam onto biological tissue parallel to the optical fiber and to reflect light received from the tissue into the optical fiber. By rotating the optical fiber, tissue along the circumference of the cavity may be examined.

Figure 3B:
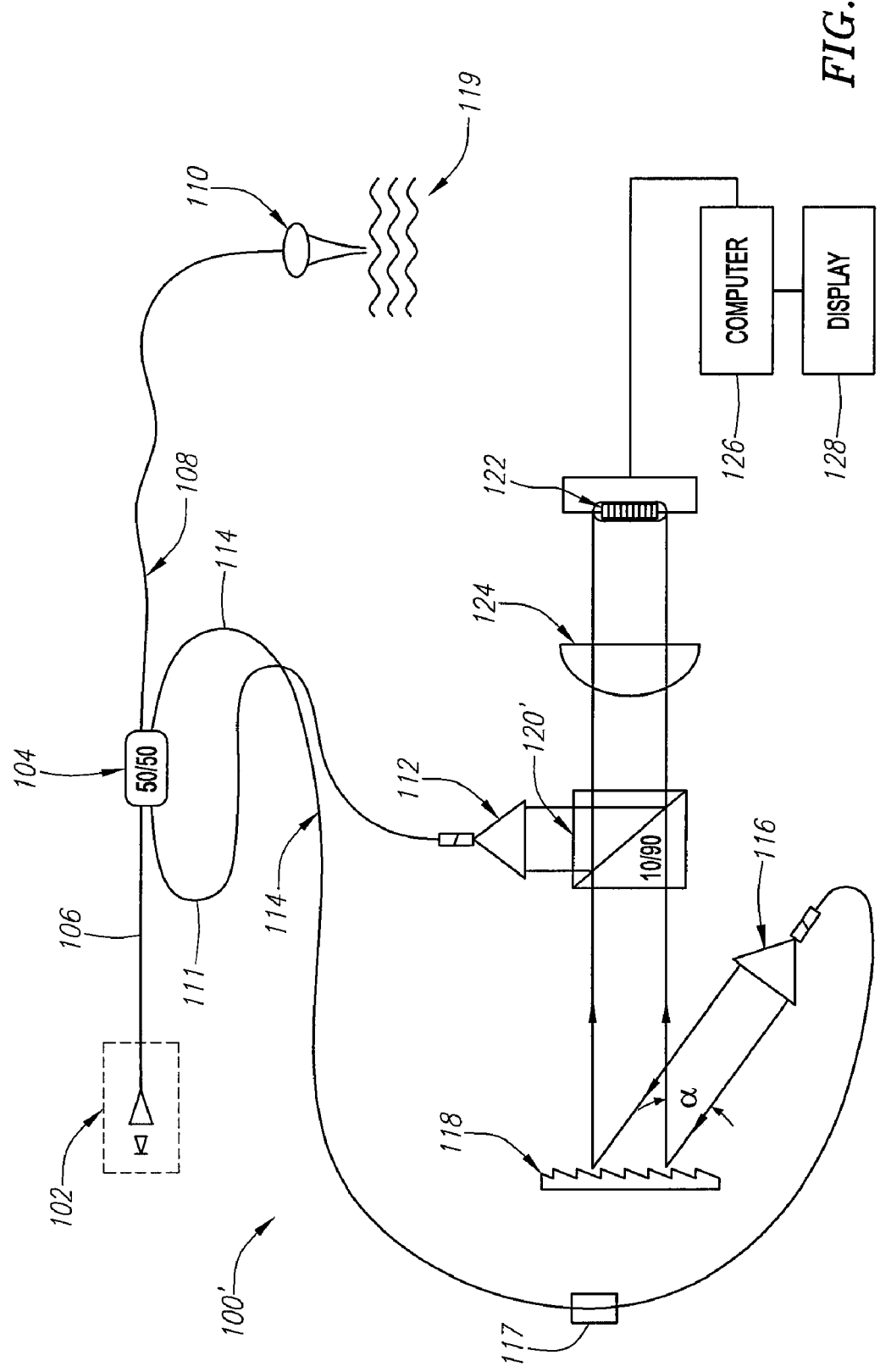
FIG. 3b is a schematic diagram of an interferometric system with a similar arrangement as the system of FIG. 3a, where both beam splitters are 50/50 beam splitters.

While it is preferred that the second beam splitter 120 in FIG. 3a be a non 50/50 beam splitter, it is not required. FIG. 3b is a schematic diagram of an interferometric system 100' that is similar to the system of FIG. 3a, except that the second beam splitter 120' is a 50/50 beam splitter. A neutral density filter or other such attenuator may be provided as needed to suppress the reference light beam to prevent saturation of the detector 124. Components common to the embodiment of FIG. 3a are commonly numbered.

Figure 4:
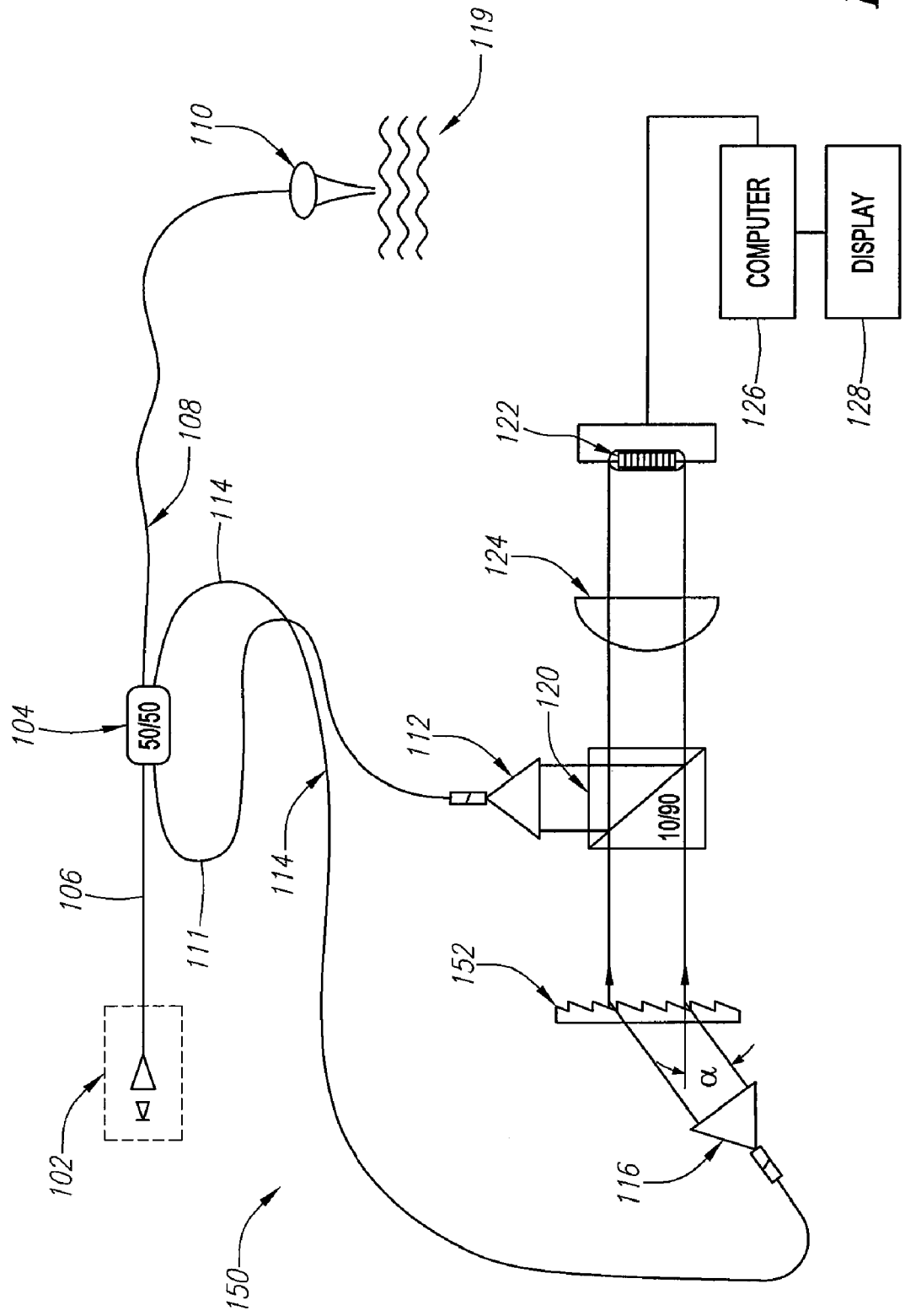
FIG. 4 is a schematic diagram of an interferometric system with a similar arrangement as the system of FIG. 3a, where the diffraction grating is a transparent diffraction grating.

FIG. 4 is a schematic diagram of an interferometric system 150 with a similar arrangement to the system 100 of FIG. 3a, except that the diffraction grating is a transparent diffraction grating 152. Components common to the configuration of FIG. 3a are commonly numbered in FIG. 4. The second collimator 116 is arranged to direct the reference light beam on a rear side of the diffraction grating 152 at an angle α. The diffracted reference beam is directed onto the open space beam splitter 120, for combination with the second sample light beam, as discussed above. The combined light beam is directed through the conjugating lens 124 and onto the multi-element detector 122, also as described above. The ability to use either a reflective diffraction grating 118 or a transparent diffraction grating 152 in the interferometric systems of the invention, adds flexibility to the design of the interferometer in practical applications. Any of the embodiments described herein can use either a reflective or a transparent diffraction grating.

Figure 5:
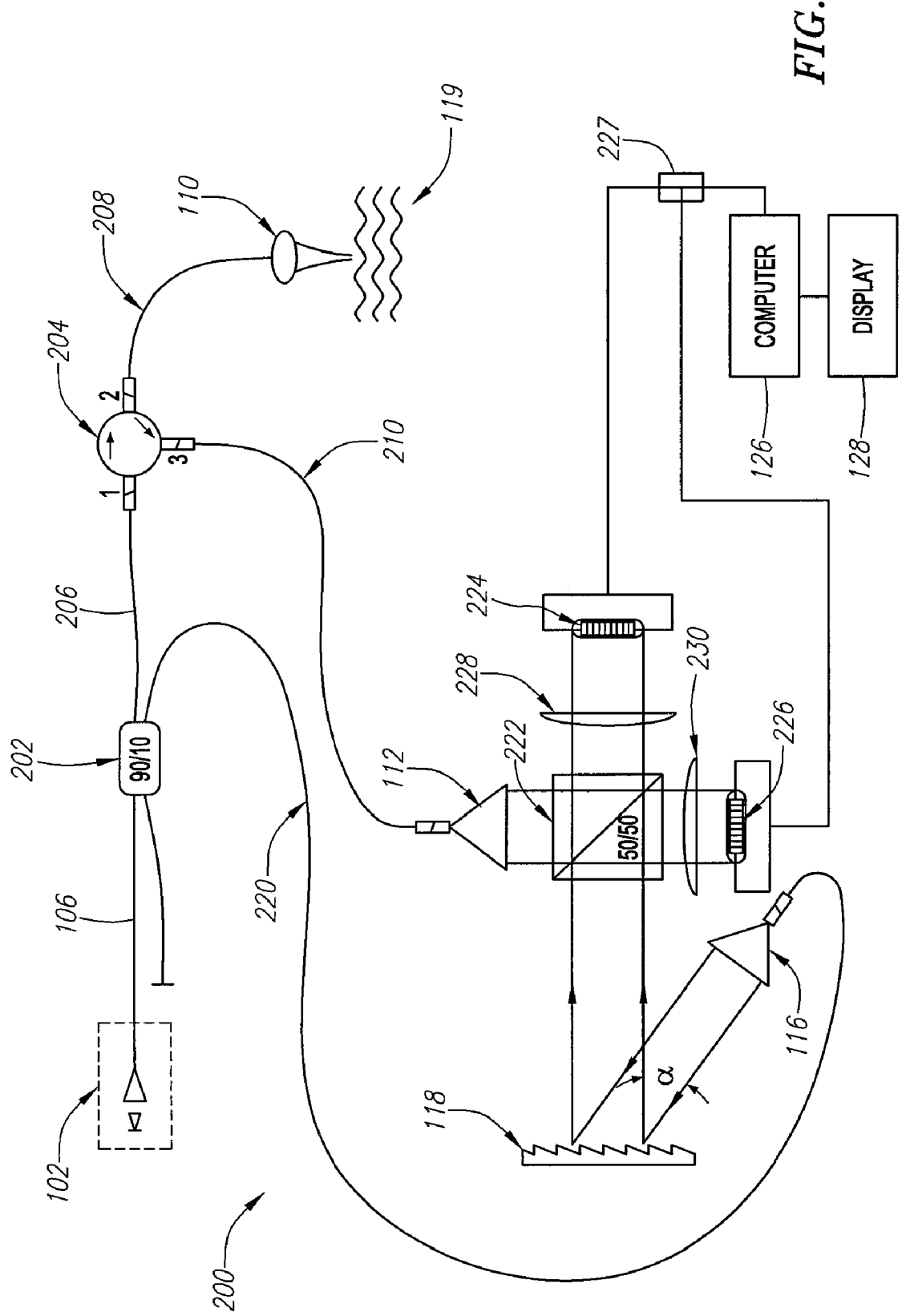
FIG. 5 is a schematic diagram of another embodiment of the invention, including an optical circulator and a first, non 50/50 beam splitter.

FIG. 5 is a schematic diagram of another embodiment of an interferometric system 200, wherein more than half of the light energy is directed into the sample light beam and less than half of the light energy is directed into the reference light beam by use of a non 50/50 fiber optic beam splitter. Preferably, substantially more than half of the light energy incident on the beam splitter, such as 75% of the energy, is directed into the sample light beam and substantially less than half of the incident light energy, such as 25%, is directed into the reference light beam. More preferably, at least about 90% of the incident light energy is directed into the sample light beam and about 10% or less is directed into the reference light beam.

Figure 1:
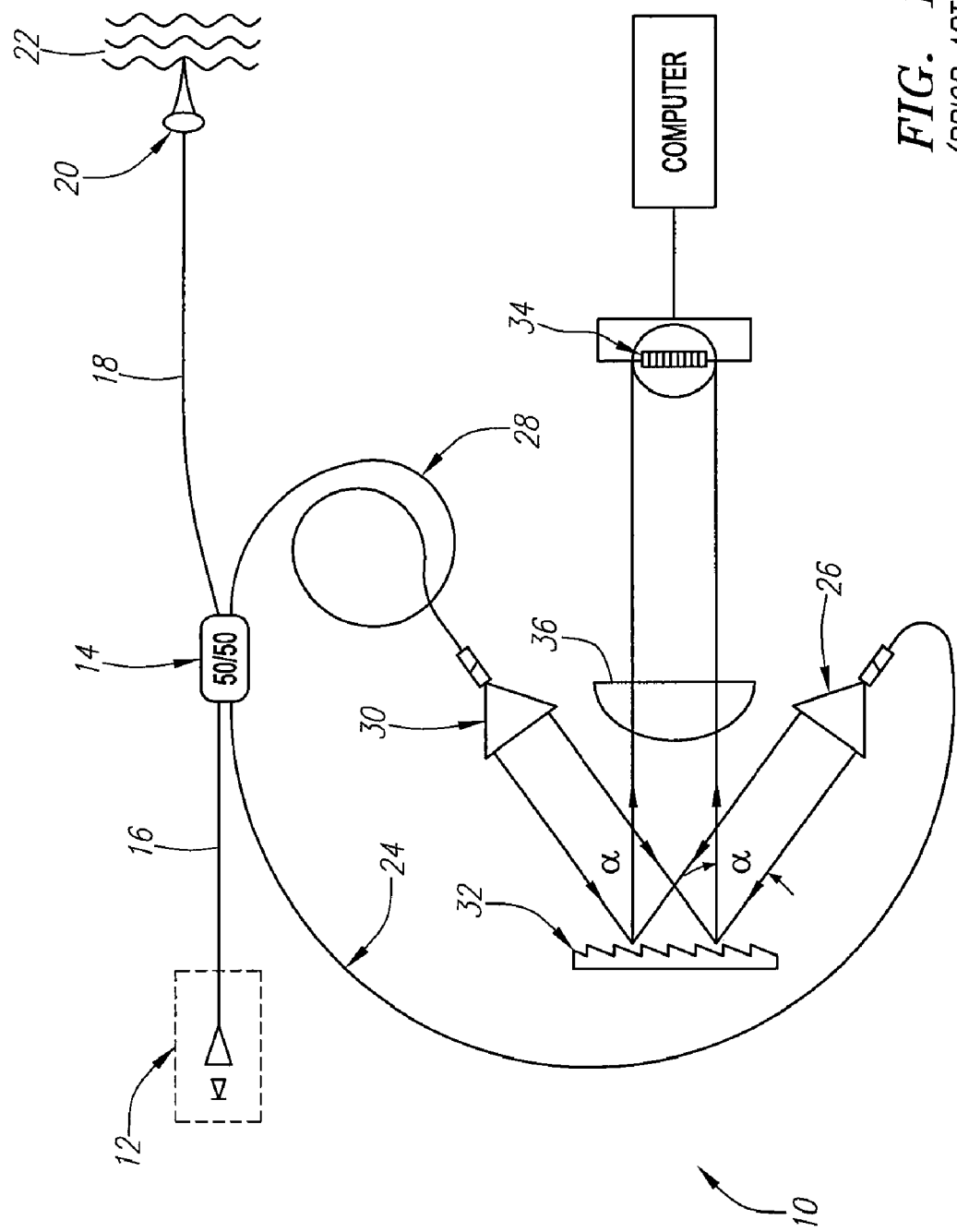
FIG. 1 is a schematic diagram of a prior art OCT system.
Figure 2:
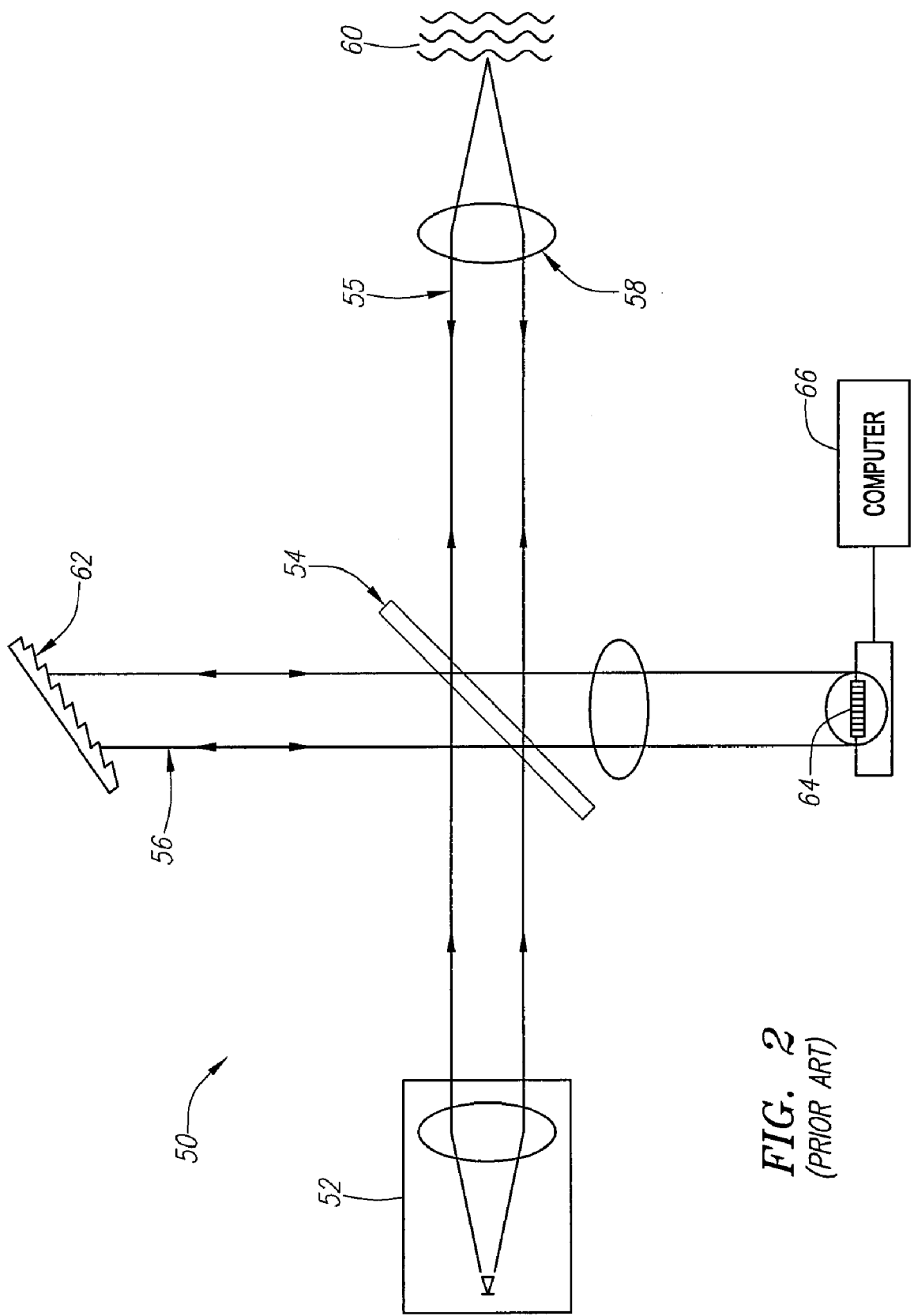
FIG. 2 is a schematic diagram of another prior art OCT system.

In this embodiment, the sample light beam is directed to and from the sample under examination through an optical circulator instead of a beam splitter, as in the embodiment of FIG. 3a and in the prior art of FIGS. 1 and 2. Therefore, the first beam splitter need not be approximately a 50/50 beam splitter.

Components common to the embodiment of FIG. 3a are commonly numbered in FIG. 5. A light source 102 provides light to a 90/10 beam splitter 202 through an optical fiber 106. The 90/10 fiber optic beam splitter 202 provides 90% of the energy of the light incident to the beam splitter 202 into the sample light beam and 10% of the energy of the light into the reference light beam.

An optical circulator 204 is provided with three ports, Port 1, Port 2 and Port 3. Light entering the optical circulator 204 through Port 1 is directed out of the circulator through Port 2. Light entering the optical circulator 204 through Port 2 is directed out of the circulator through Port 3. An optical fiber 206 is optically coupled to the first beam splitter 202 to Port 1 of the optical circulator 204 to convey the sample light beam to the circulator.

An optical fiber 208 is optically coupled to Port 2 of the optical circulator 204 and to a focusing lens 110. An optical fiber 210 is optically coupled to Port 3 of the optical circulator 204 and to a first collimator 112. The sample light beam is conveyed from the first beam splitter 202 to Port 1 of the optical circulator 204 through the optical fiber 206. The sample light beam is directed to Port 2 of the optical circulator, where it exits the circulator and is conveyed to the focusing lens 110 by the optical fiber 208. The focusing lens focuses the sample light beam onto the sample 119. Light received from the sample is focused and coupled into the optical fiber 108, forming a second sample light beam to be returned to Port 2 of the optical circulator. The second sample light beam is directed from Port 2 to Port 3 of the optical circulator, where it is conveyed by the optical fiber 204 to the first collimator 112.

An optical fiber 220 is also optically coupled to the beam splitter 202 and to a second collimator 116, as in the embodiment of FIG. 3a. A reference light beam having 10% of the energy of the light conveyed to the 90/10 beam splitter 202 from the light source 102 is directed into the optical fiber 220. The second collimator 116 directs the reference light beam onto a reflective diffraction grating 118. The diffraction grating 118 introduces an optical path difference to the reference light beam and reflects the diffracted reference light beam onto the open space beam splitter 120. A transparent diffraction grating 152 could be used instead of the reflective diffraction grating 118, as discussed above. The first collimator 112 also directs the second sample light beam onto the open space beam splitter 120 for combination with the reference light beam.

In this embodiment, the second beam splitter 120 is approximately a 50/50 beam splitter 222. Preferably, the second beam splitter 120 is a 50/50 beam splitter. Two combined sample/reference beams, each having half of the energy of the second sample light beam and half of the energy of the reference light beam, are formed. Two photo detectors 224, 226, which are preferably multi-element photo detectors, are provided, one along the path of each combined light beam. Because two detectors are provided, the 50/50 beam splitter 222 does not cause a loss of energy and information in the second sample light beam. Respective conjugating lenses 228, 230 are provided between each detector 224, 226 and the second beam splitter 222. The outputs of individual detectors in corresponding spatial positions in each array are combined by analog circuitry 227. The output of the analog circuitry 227, which may be parallel or serial, is provided to a signal processor, such as the computer 126, for processing into an image in a manner known in the art. As noted above, the analog circuitry 227 may convert the signals output from the detectors 224, 226 into digital signals, as well. Two detectors may be readily provided in the embodiment of FIG. 3b, as well, in the same manner.

Preferably, about 90% or more of the light energy is directed into the sample light beam and about 10% or less of the light energy is directed into the reference light beam by the first beam splitter 202. The amount of energy provided to the sample and reference beams may be controlled by selection of the characteristics of the fiber optic beam splitter 202 so that only the necessary amount of light energy is provided to the reference light beam to sufficiently amplify the sample light beam for imaging without saturating the multi-element photo detectors 224, 226. The remainder of the energy is directed to the sample light beam. A 2/98, a 95/5 or a 1/99 or other such beam splitter may also be used, for example.

Directing the second sample light beam received from the sample 119 through the optical 204 circulator 204 instead of back through the first beam splitter 202 avoids a significant source of loss in the second sample beam. The loss in the optical circulator is between about 0.5 decibels ("db") to about 1.1 db each way. The two way loss in the optical circulator is therefore about 1.0 db to about 2.2 db (about 37%). The loss in a 50/50 beam splitter 222, by contrast, is 50% each way or 75% if the sample beam travels through the 50/50 beam splitter twice.

The detectors 224, 226 may be tuned to detect light at the same wavelength band or at different wavelength bands. The ability to detect more than one wavelength band is useful for spectroscopy and for reducing aliasing in the image.

Figure 6:
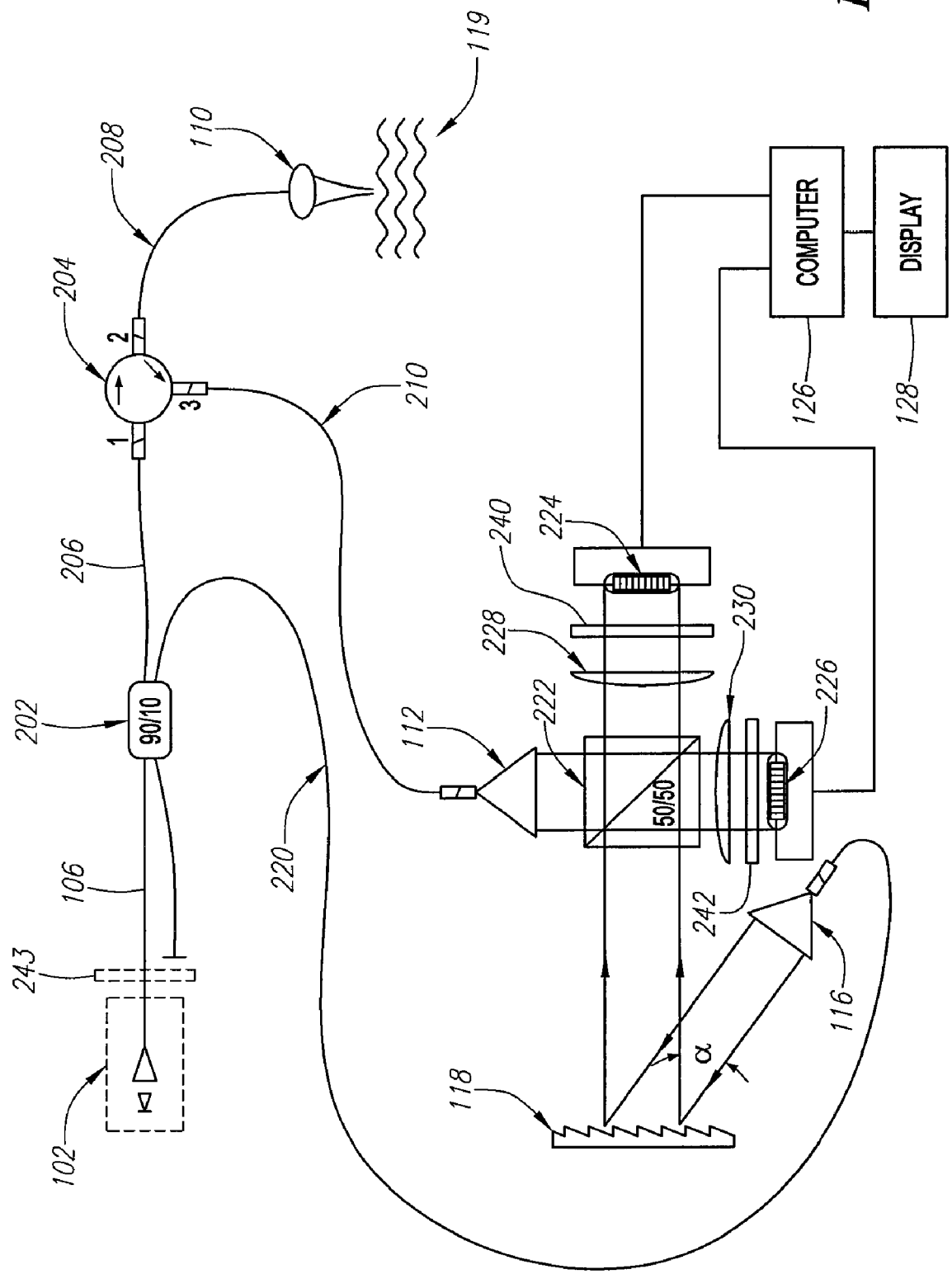
FIG. 6 is a schematic diagram of the system of FIG. 5, including polarization filters for use in detecting polarization related information.

The two combined sample/reference light beams in the embodiment of FIG. 5 may contain polarization related information. Birefringence measurements may be made by providing a polarization filter along each light beam, where each filter allows passage of light having a different polarization. In FIG. 6, polarization filters 240, 242 are shown between each of the conjugating lenses 228, 230 and the detectors 224, 226, respectively. The outputs of each detector 222, 224 may be provided to the computer separately, for processing. Two images may be displayed. Differential measurements may be made by comparing the signals at each detector as a function of spatial position and relative intensity, as is also known in the art. Variations in intensity versus position are an indication of polarity sensitive areas of target tissue. The optical fiber used in this embodiment is preferably a polarization maintaining (high birefringence) optical fiber, as is known in the art. A polarization filter 243, shown in phantom, may also be provided between the light source 102 and the fiber optic beam splitter 202 instead of the polarization filters 240, 242, to polarize the light beam emitted by the light source to a desired polarization. Instead of the polarization filter 243, the second beam splitter 222 may be a polarization beam splitter. A single detector, as in the embodiments of FIGS. 3 and 4, may also be used to detect a light beam of a particular polarization.

Polarization filters may be provided in other interferometric systems where two combined beams are formed, as well. For example, a 50/50 beam splitter may also be provided between the diffraction grating 32 and the detector 34 in the system of the '133 patent shown in FIG. 1, to form two combined beams. A second detector, two polarization filters and two conjugating lenses may then be provided, as in FIG. 6, to conduct birefrigence measures.

Figure 7:
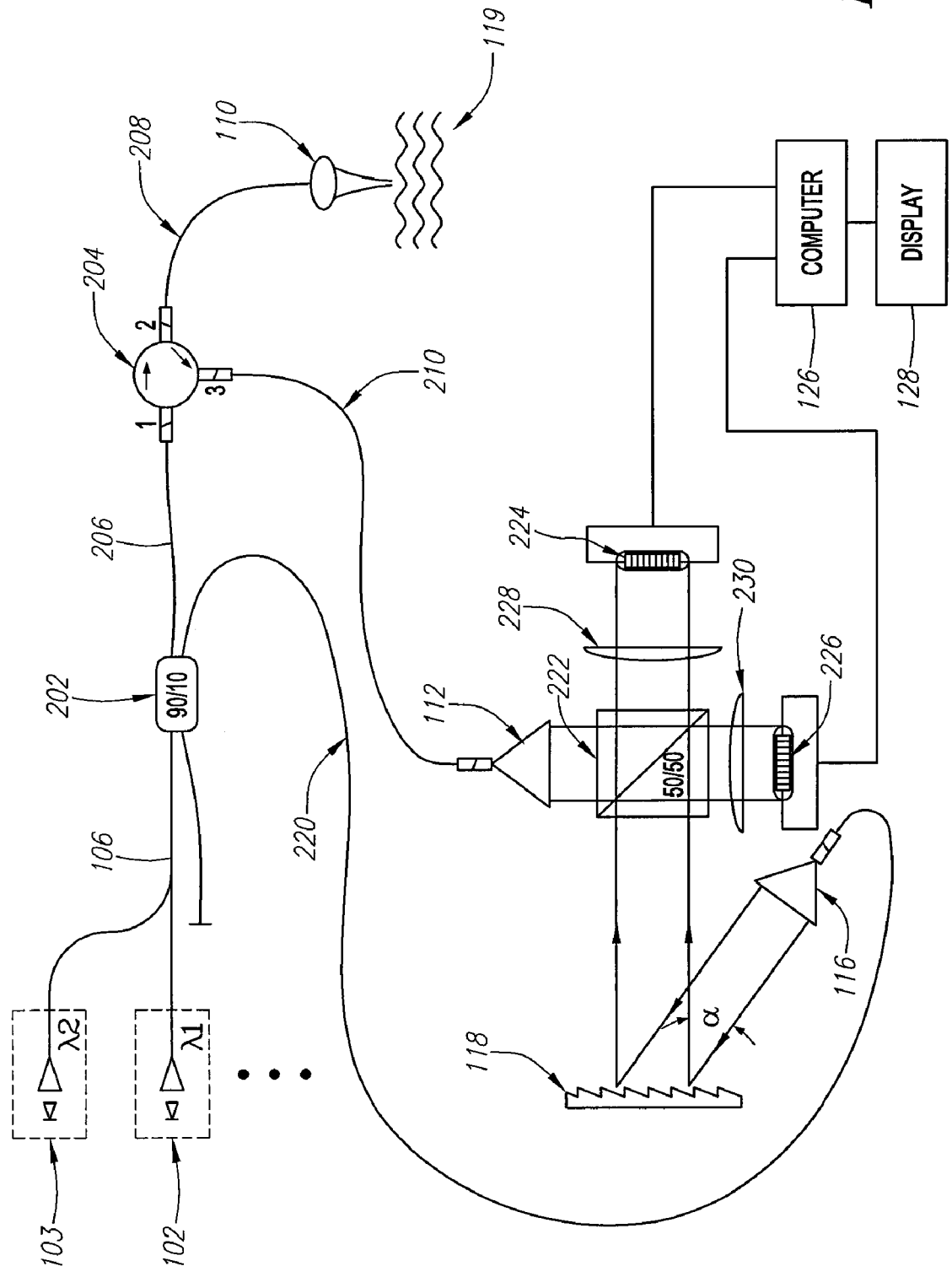
FIG. 7 is a schematic diagram of the system of FIG. 5, including multiple light sources.

In another variation in the embodiment of FIG. 5, a second light source 103 may be provided, as shown in FIG. 7. Additional light sources may also be provided. Each light source may emit light at a different wavelength. For example, the first light source can emit light at 800 nanometers and the second light source can emit light at 1200 nanometers. The light from the second light source 103 may be coupled into the optical fiber 106 by a wavelength division multiplexor, for example. One of the detectors 224, 226 may be tuned to detect light at a wavelength corresponding to the first light source 102 and the other detector may be tuned to detect light at a wavelength band corresponding to the second light source 103. If more than two light sources are provided, the individual photo detectors in each array can be tuned to detect light at different wavelength bands. Bandpass filtering, detector response and the fiber characteristics of each "detection channel" may be selected to optimize the use of specific wavelengths. The outputs of each detector 222, 224 may be provided to the computer separately for processing. Two or more images may be displayed. The interference patterns at each wavelength band may be compared as a function of spatial position and intensity at each wavelength band. The difference in intensity at the same position in the interference patterns may indicate wavelength dependent attenuation or absorption of the sample.

Fluorescence of tissue is known to be dependant upon tissue type and tissue constituents. One of the light sources in FIG. 7 may be in the blue or ultraviolet range, for example, to induce fluorescence in the tissue. One of the detectors 224, 226 may be tuned to the ultraviolet, blue or other wavelength band at which the target tissue is expected to fluoresce to detect the intensity of the emitted fluorescent light.

Figure 8:
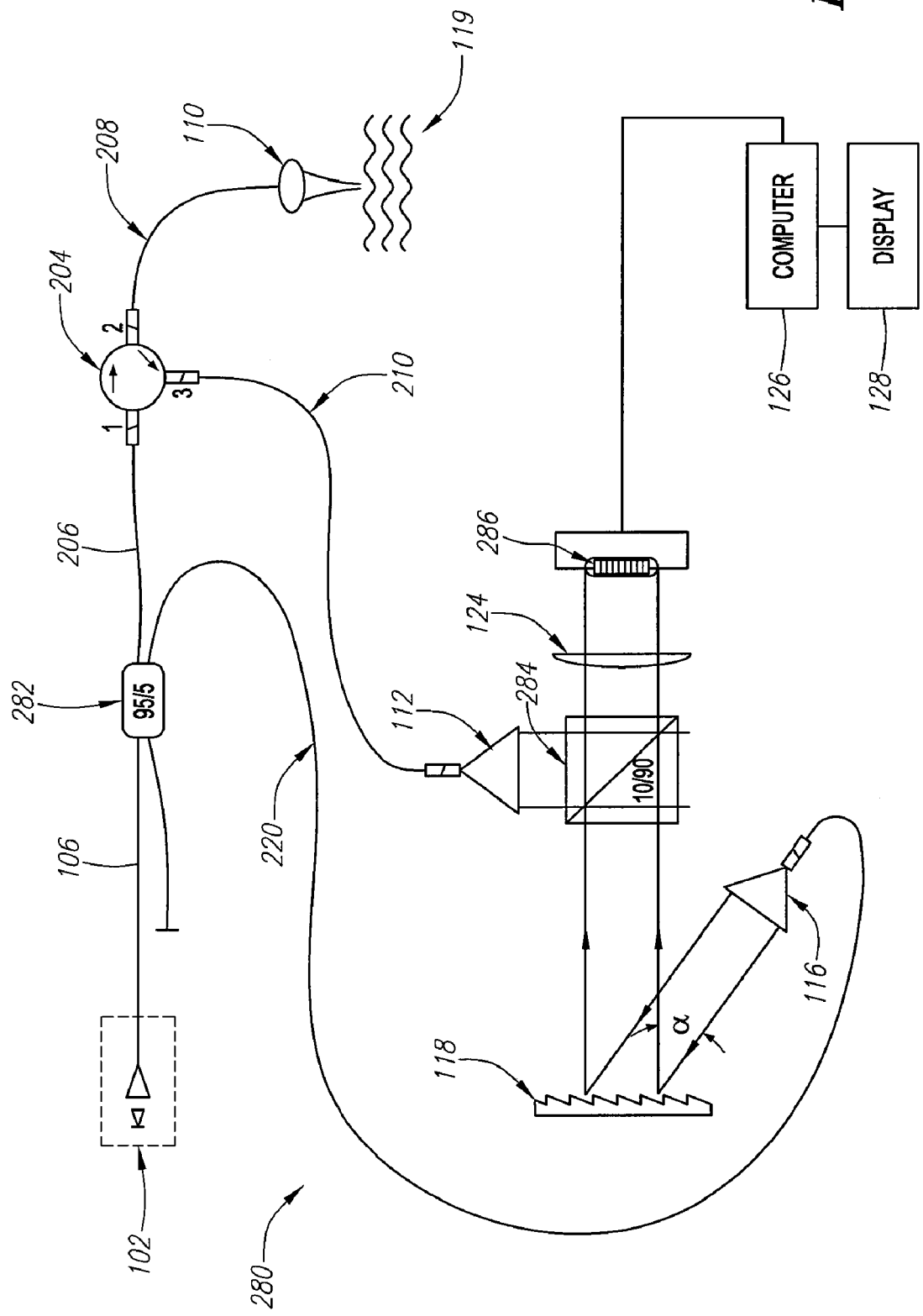
FIG. 8 is a schematic diagram of the system of FIG. 5, including an optical circulator and two non 50/50 beam splitters.

In another embodiment using an optical circulator 204, neither the first fiber optic beam splitter nor the second open space beam splitter is a 50/50 beam splitter. In the system 280 of FIG. 8, the first beam splitter 282 is a 95/5 beam splitter, for example, that directs 95% of the light energy provided to the beam splitter into the sample light beam and 10% into the reference light beam. The second open space beam splitter 284 is a 10/90 beam splitter, for example, directing 90% of the light energy in the second sample light beam and 10% or less of the light energy in the reference light beam toward a single detector 286 in the combined beam. Varying the characteristics of both beam splitters 282, 284 provides additional flexibility in optimizing the energy distribution between the sample and reference light beams. Components of the system 280 common to the embodiments of FIGS. 5 and 3a are commonly numbered.

To determine the theoretical percentage of the light source energy reaching the detector from the sample arm in the various embodiments of the invention and in the prior art, the sample under examination may be replaced by a mirror. The Table below shows the percentage of the light source energy in the sample and reference arms at the sample, at the diffraction grating and at the detector in the prior art interferometer of FIG. 1 and in the example interferometers of FIGS. 3a, 4 and 5, if the sample light beam is reflected by a mirror (suffers no loss due to interaction with the sample).

| Figure | Percentage of light source energy incident on: | | | | |
|--------|Sample|Diffraction Grating| |Detector/Detectors| |
| | Sample Arm | Sample Arm | Reference Arm | Sample Arm | Reference Arm |
| FIG. 1 | 50 | 25 | 50 | 12.5 | 25 |
| FIG. 3a | 50 | NA | 50 | 22.5 | 2.5 |
| FIG. 4 | 50 | NA | 50 | 22.5 | 2.5 |
| FIG. 5 | 90 | NA | 10 | 56.7 | 5 |

In the prior art of FIG. 1, the light energy in the reference light beam incident on the detector is 25% of the light energy from the source and is higher than the sample light energy. To prevent saturation of the detector, the reference beam has to be suppressed. In the embodiments of FIGS. 3a and 4, in the sample arm, the light source energy is reduced by 75% by two passes through the 50/50 beam splitter and then by 10% by the 10/90 beam splitter. In the reference arm, the light source energy is reduced by 50% by the first beam splitter, 50% by the diffraction grating and 90% by the second beam splitter. In the embodiment of FIG. 5, in the sample arm, the light source energy is reduced by 10% by the 90/10 beam splitter and by 37% by two passes through the optical circulator. The loss caused by the 50/50 beam splitter does not reduce the total energy of the sample light beam because the total energy of the light incident on both detectors by the sample light beam is the same as the energy of the sample light beam incident on the beam splitter. In the reference arm, the light is reduced to 10% of the light energy from the source by the 10/90 beam splitter and then by 50% by the diffraction grating. In the embodiments of FIGS. 3a, 4 and 5, the proportion of the initial light energy in the reference light beam incident on the detector is much lower than in the prior art and the proportion of the light energy in the sample light beam is higher. Saturation of the detector or detectors may be readily avoided by suitable selection of the characteristics of the beam splitters. A neutral density filter may be provided along the reference arm for more precise control over the energy of the reference light beam, if necessary. Since more of the light energy from the source may be allocated to the sample light beam, where it is most needed, less energy is wasted in the system.

Figure 9:
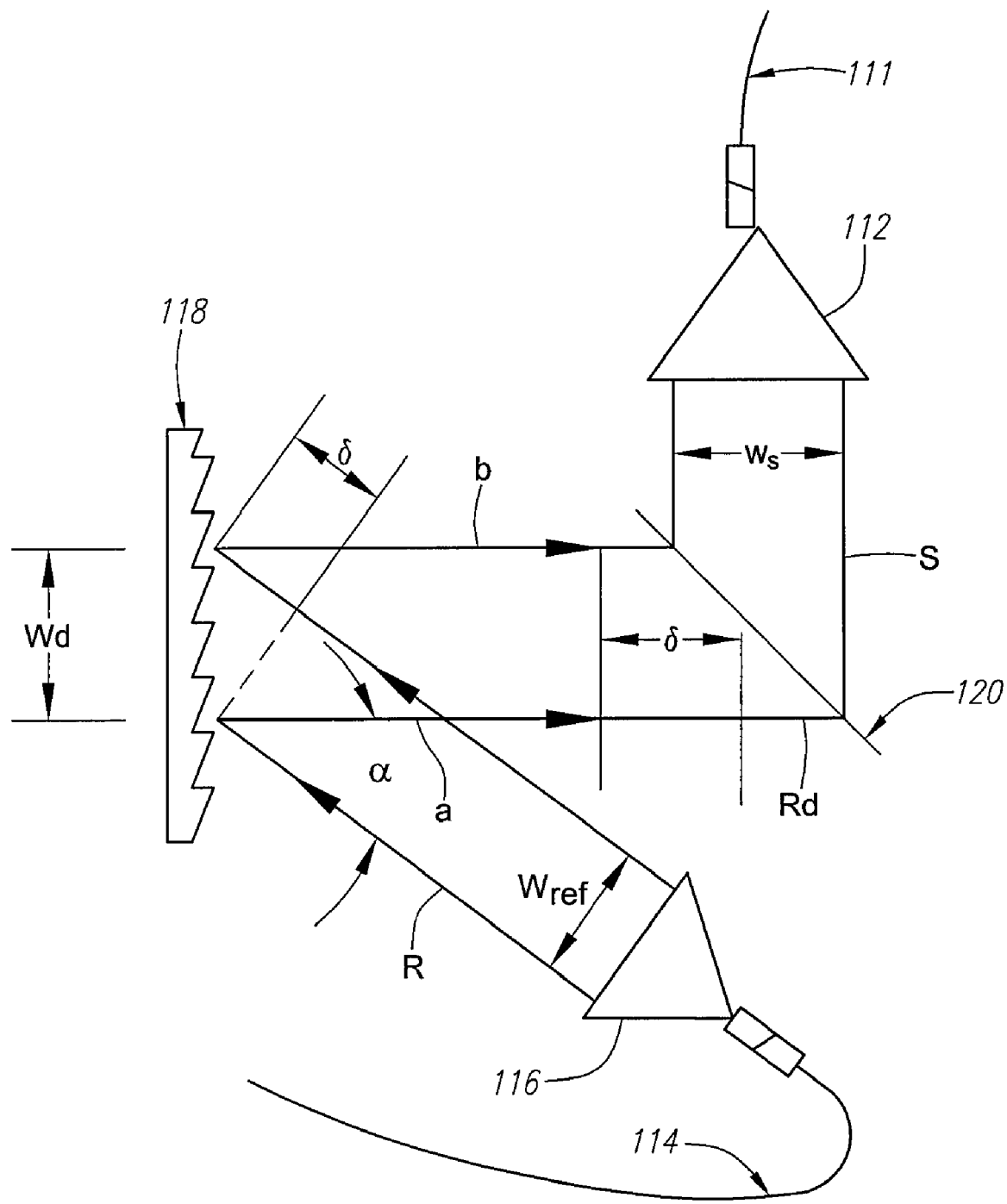
FIG. 9 is an enlarged view of the reference light beam being diffracted by the diffraction grating, indicating the optical path difference across the reference beam.

FIG. 9 is an enlarged view of the reference light beam R emitted by the collimator 116 being diffracted by the diffraction grating 118, showing the maximum optical path difference δ across the diffracted reference light beam Rd for the embodiment of FIG. 3a. The second sample light beam S received from the sample is shown being emitted by the collimator 112. The second beam splitter 120 is also shown. The optical path difference δ varies gradually across the diffracted reference light beam Rd such that the difference at one side of the beam cross-section "a" is about zero and the difference at the opposite side of the beam "b" is the maximum difference δ. The maximum optical path difference δ is typically chosen to enable measurement of the light scattered from the desired depth. Since the optical paths of the reference and sample light beams have to be substantially equal, the optical path difference δ corresponds to the depth of the image in the second sample light beam S, corrected by the refractive index of the media in which the depth is measured. The maximum optical path difference δ is a function of the width Wd of the diffracted light beam and the angle of incidence α:

$$\delta = W_d \times \sin \alpha. \quad (1)$$

The depth Δ is a function of the maximum optical path difference δ. Since it takes a two-way sample beam path to determine the depth versus a one way reference beam path to define the maximum optical path difference, the depth is half of the maximum optical path difference δ. Since the depth Δ is measured in a material other than air, it is also a function of the refraction coefficient of the sample material η:

$$\Delta = \delta/2\eta. \quad (2)$$

The angle of incidence α of the reference light beam on the diffraction grating is a function of the diffraction grating parameter p (distance between adjacent grooves) and the light wavelength λ. The diffraction grating formula is:

$$\sin \alpha = \lambda/p. \quad (3)$$

Also, as shown in FIG. 9, the width Wref of the reference light beam R is less than the width Wd of the diffracted reference light beam Rd. Preferably, the width Wd of the diffracted reference light beam is the same as the width Ws of the second sample light beam S. The combined light beam (not shown) has the same width. The width Wref of the reference light beam is therefore preferably:

$$W_{ref} = W_s/\cos \alpha. \quad (4)$$

The width of the detector array or arrays should the same or slightly greater than the width of the combined light beam. Preferably, the first collimator 112, that collimates the second sample light beam S received from the sample, has the same dimensions as that of the detection array.

For example, if the sample is biological tissue (η=1.33) and the depth of measurement is Δ=3 mm, the maximum optical path difference from formula (2) would be: δ= 7.98 mm. If the light source has a wavelength λ=820 nm and the diffraction grating parameter is p=1/830 mm, the angle α from formula (3) would be: Sin α=0.697 (α=44.2 deg.). Then, the width Wd of the diffracted reference beam Rd, which is preferably equal to the width Ws of the second sample light beam received from the sample Ws from (1) would be Wd=11.45 mm. The width of the combined light beam is also Wd. The photo detector array would then also have a width of at least 11.45 mm.

In the embodiments above, the light source 102 is a low coherence, broadband light source, such as a super luminescent diode. The coherence length of the light source may be from about 15 to about 30 microns, for example. The wavelength may be between about 800 to about 1500 nanometers, for use with biological tissue. The light source should emit light at a power of at least about 10 milliwatts for depth measurements of about 1 millimeter. The light source should emit light at a power of at least about 50 milliwatts for depth measurements of 2-3 millimeters. Superluminescent diodes for use in the embodiments may be obtained from Super Lume Diodes, Ltd. Moscow, Russia, or Hamamatsu Photonics K.K., Solid State Division, Hamamatsu City, Japan, ("Hamamatsu") for example.

The detector is preferably a multi-element photo detector, such as a photo diode array. An avalanche mode photo diode array may be used, for example The photodiode array preferably has at least 256 diodes. An array of 512 photo diodes or more is more preferred. Photo diode arrays may be obtained from Sensors Unlimited, Inc., Princeton, N.J. and Hamamatsu, for example. A charge-coupled device ("CCD") may also be used.

Appropriate optical fibers and fiber optic beam splitters of desired characteristics are readily commercially available. They may be obtained from Corning Incorporated, Corning, N.Y., for example. Open space beam splitters of desired characteristics are also readily commercially available. They may be obtained from Edmunds Scientific, Tonawanda, N.Y., for example. The conjugating lenses and focussing lens may also be obtained from Edmunds Scientific, for example.

Figure 10:
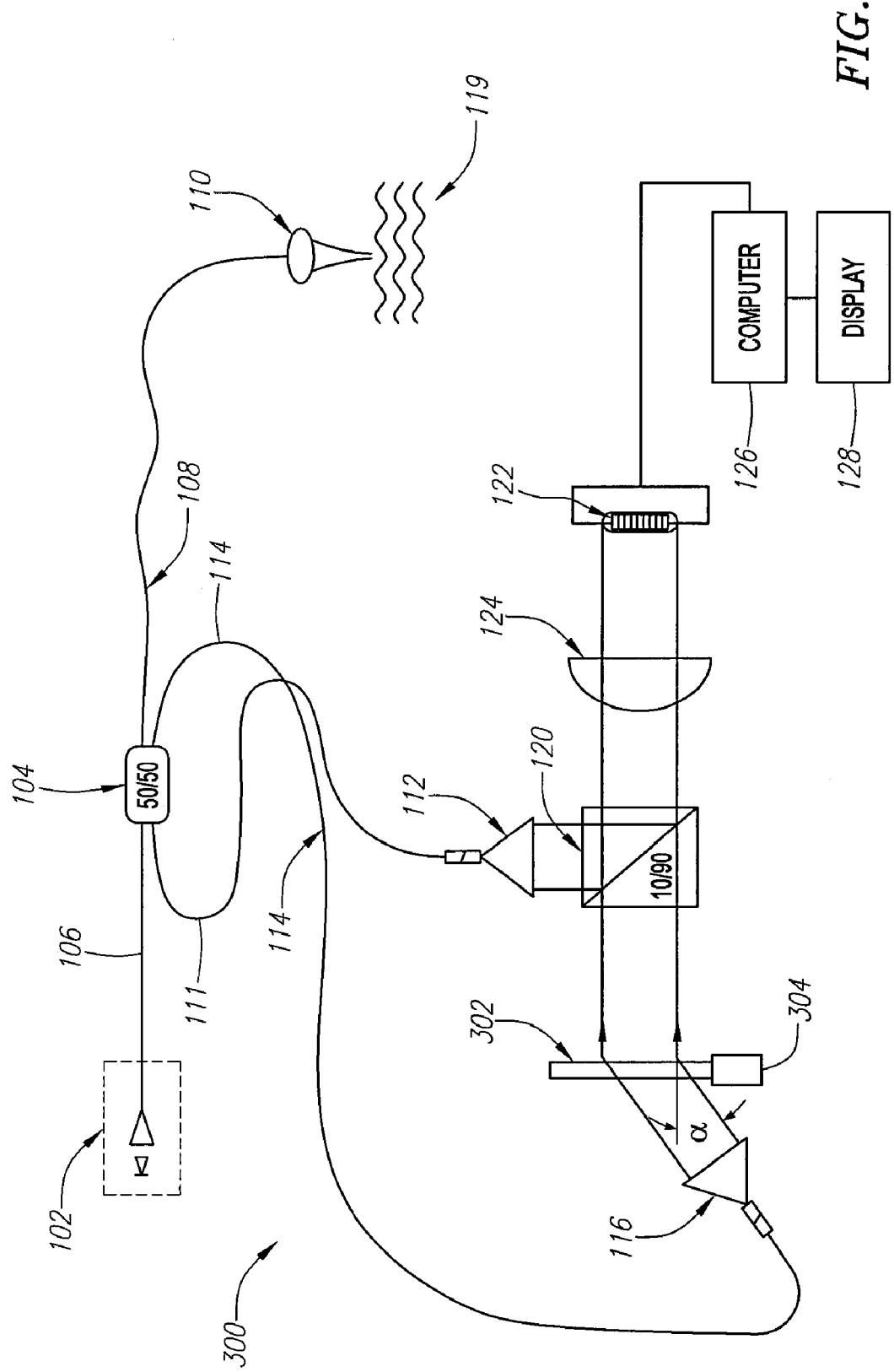
FIG. 10 is a schematic diagram of an interferometric system in accordance with another embodiment of the invention, wherein an acousto-optic modulator ("AOM") acts as both a transparent diffraction grating to introduce an optical path difference and as a modulator.

FIG. 10 is yet another embodiment of an interferometric system 300, wherein an acousto-optic modulator ("AOM") 302 acts as both a transparent diffraction grating to introduce an optical path difference to the reference light beam and as a modulator to introduce a frequency shift. Otherwise, the system is the same as the embodiment of FIG. 3a. One AOM may be used for shallow depths of a few hundred microns, for example. Two modulators may be used for greater depths of 500 to 1,000 microns, for example. One AOM may also be used along with a transparent diffraction grating, as shown in U.S. Pat. No. 6,114,645, which is incorporated by reference herein. While one AOM may introduce a frequency of modulation higher than that desirable in an OCT system, two or more AOM's in series, each driven at different frequencies, may be used to achieve the desired frequency. The AOM 302 may be driven by a programmable signal generator, as is known in the art.

Since the projected interference pattern generated by the interferometric system of the invention is formed on the detector nearly instantaneously, pulsed imaging may also be implemented in any of the embodiments discussed above.

Pulsed imaging allows for the use of higher peak power and lower average power (lower duty cycle), enabling increased penetration through attenuative structures while maintaining low average light energy for safe operation. A laser diode may be used in a pulsed mode as the light source in any of the embodiments. The laser diode may be smaller and less expensive than the superluminescent diode discussed above for continuous operation, because a small laser diode may produce a sufficient peak output at a wider bandwidth in a pulse mode without being destroyed.

Figure 11:
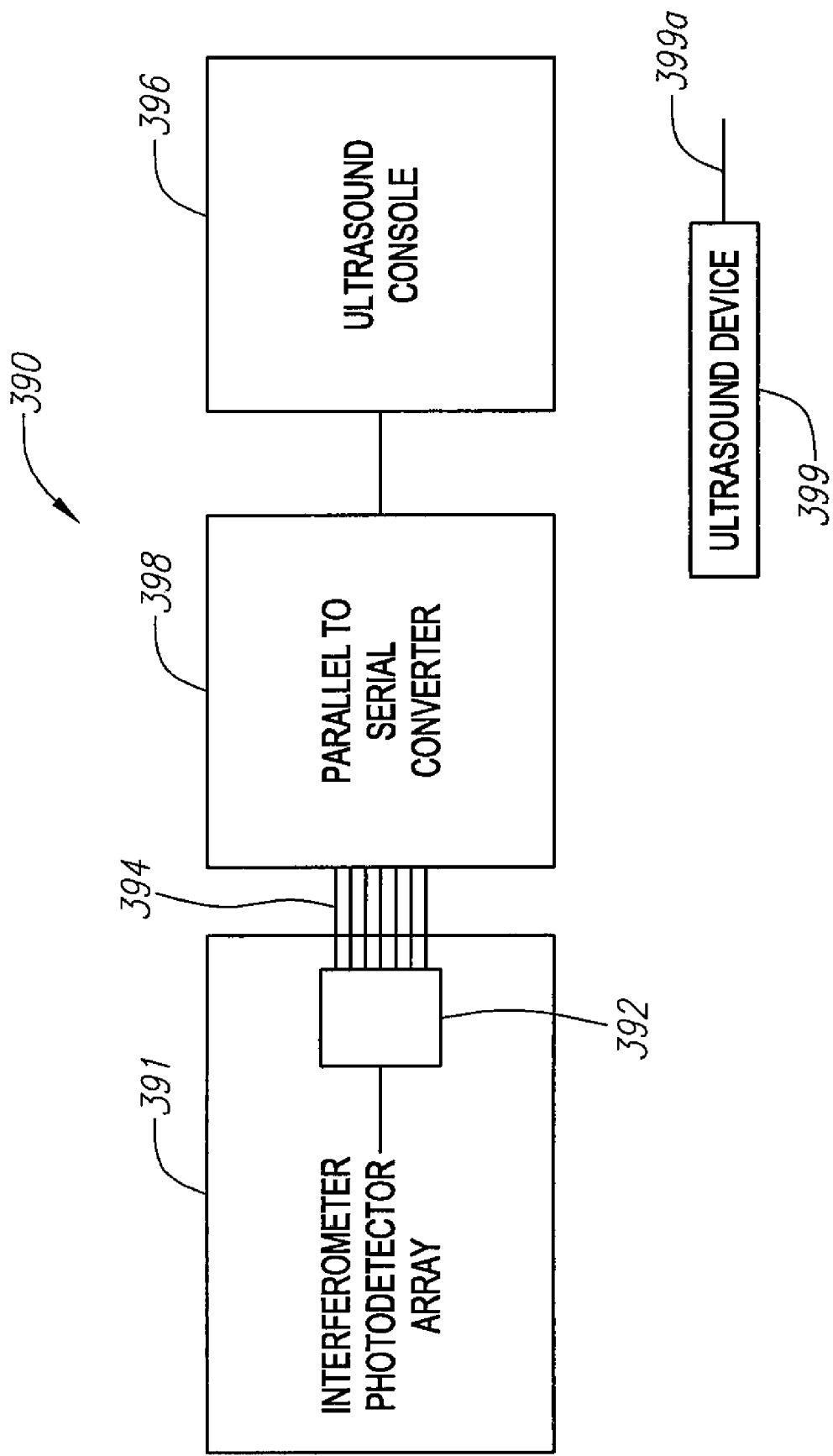
FIG. 11 is a schematic diagram of an interferometer connected to an ultrasound console.

As discussed above, the output of the detector or detectors in the embodiments above may be analyzed in a conventional manner to produce an image. The output may also be analyzed by the same algorithms used to process ultrasound data. FIG. 11 is a schematic diagram of an imaging system 390 comprising an interferometer 391 including a photo detector array 392 with a plurality of parallel outputs 394 connected to an ultrasound console 396 through a parallel to serial converter 398. An ultrasound device 399 is also shown, with an output 399a. The output 399a of the ultrasound device 399 may also be connected to the ultrasound console, in the same or a different input than the interferometer 391. A doctor or technician may thereby use either the interferometer 391 for optical imaging or the ultrasound device 399 for ultrasound imaging, with the same ultrasound console. The parallel to serial converter 398 is discussed further below. First, ultrasound imaging is briefly discussed.

Ultrasound medical imaging is a commonly used procedure to produce images of body cavities such as blood vessels and surrounding tissue. To image a blood vessel and surrounding tissue through ultrasound, an Intravascular Ultrasound ("IVUS") catheter is typically inserted into the blood vessel in a known manner. An example of an IVUS catheter may be found in U.S. Pat. No. 5,715,825, entitled Acoustic Imaging Catheter and the Like, incorporated by reference herein.

In ultrasound imaging, an ultrasound transducer is supported at the distal end of an IVUS catheter, for example. The transducer emits ultrasound waves in the blood vessel or other such cavity when excited by a pulse. A portion of the emitted ultrasound waves is reflected back to the ultrasound transducer by tissue boundaries. The reflected ultrasound waves induce an echo signal at the ultrasound transducer. The echo signal is transmitted from the ultrasound transducer to an ultrasound console, which typically includes an ultrasound image processor, such as a computer, a microprocessor or a microcontroller, and a display. The display may comprise a monitor and/or a printer. The ultrasound console uses the received echo signal to image the cavity. An ultrasound system including an ultrasound image processor and display is available from Boston Scientific Corporation, Natick, Mass.

The echo signal is a serial amplitude modulated signal in which the amplitude of the signal varies with time. A typical echo signal has a time length of 8 μs, which corresponds to an image depth of approximately 6 millimeters from the ultrasound transducer. The echo signal carries both image brightness information and image depth information, where depth may be taken with respect to the ultrasound transducer. The image brightness information is provided by the amplitude of the echo signal. The image depth information is provided by the time position within the echo signal. An earlier time position in the echo signal corresponds to a lower image depth than a later time position in the echo signal.

In applicants' improved interferometric systems discussed above, as well as in other OCT systems using an array of photo detectors, the array captures image brightness information at multiple image depths in one instance. Since the detected spatial information may be read and stored, the parallel channel outputs of the photo detector array of the interferometric system may be processed into a serial analog or serial digital signal by a parallel to serial converter. The resulting serial signal carries image brightness information and image depth information in a similar manner as a typical echo signal. The time length and/or frequency of the serial signal may be adjusted to better match the time length and/or frequency of a typical echo signal that the ultrasound console is configured to receive by synchronizing the signal to the sweep speed of the ultrasound device (speed of rotation of the transducer) and to the propagation velocity of sound. This enables an ultrasound console to process the serial analog signal into an image, in the same way ultrasound data is processed. The same ultrasound console may thereby be used to process both ultrasound based images derived from data received from an ultrasound catheter and optical interferometric based images derived from data received from an interferometric catheter, thereby reducing the cost of having both ultrasound imaging and optical imaging capabilities.

Figure 12:
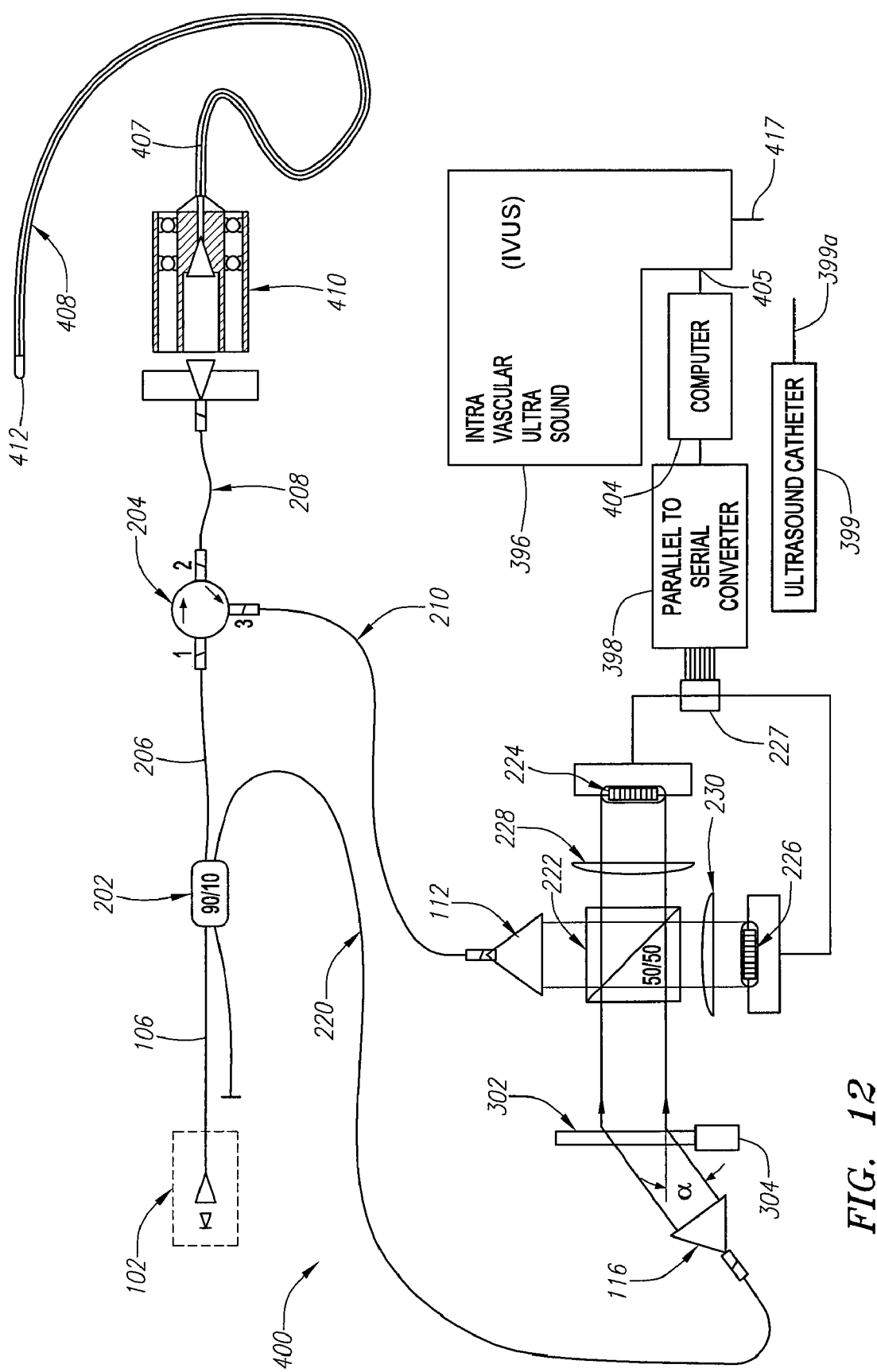
FIG. 12 is a schematic diagram of an AOM based interferometric system, as in the embodiment of FIG. 10, coupled to an ultrasound console.

FIG. 12 shows an AOM based interferometric system 400, as in the embodiment of FIG. 10, wherein the first, fiber optic beam splitter 202 is a 90/10 beam splitter and the second, open space beam splitter 222 is a 50/50 beam splitter. Two photo detector arrays 224, 226 are provided, as in the embodiment of FIG. 5. The outputs of corresponding detectors in each of the parallel outputs from the photo detector arrays 224, 226 of the interferometric system 400 are combined by analog circuitry 227, as discussed. The parallel outputs of the analog circuitry 227 are input to a parallel to serial converter 398 that converts the parallel outputs into a serial amplitude modulated signal that can be processed by an ultrasound console. If only one detector is provided, as in the embodiment of FIG. 3a, for example, the analog circuitry 227 is not needed and the parallel outputs of the photo detector array 122 could be provided directly to the parallel to serial converter 398.

A computer 404 may optionally be provided to process the serial signal output by the parallel to serial converter. The serial signal is then provided to the IVUS console 396 through an input 405 for processing into an image for display. The IVUS console comprises a signal processor, such as a computer, a microprocessor or a microcontroller, and a display to display generated images, as is known in the art. The interferometer may be selectively connected to the input 405 when optical imaging is desired. An ultrasound catheter 399 is also shown in FIG. 12, with an output 399a. The output 399a may be connected to the input 405 or a separate input 417 of the IVUS console 396 when ultrasound imaging is desired.

The other embodiments of the interferometric systems, as well as other interferometric systems, could be used with the IVUS console, as well.

The optical fiber 208 of the sample arm is shown coupled to an optical fiber 407 within a catheter 408 through a rotary connector 410. A mirror or prism 412 is shown for reflecting the sample light beam out of the catheter to tissue in a body cavity, as described above. The rotary connector 410 is driven by a motor, as is known in the art.

The parallel to serial converter may be one of the electronic interfaces described in U.S. patent application Ser. No. 09/909,357 ("the '357 application"), entitled "Electronics Interface for an Ultrasound Console", filed on Jul. 18, 2001, assigned to the assignee of the invention and incorporated by reference herein.

The ultrasound console 396 may be configured to receive either an analog or a digital input. In one example of an electronics interface disclosed in the '357 application for receiving a analog input, the electronics interface comprises a plurality of channel processors, each coupled to one of the parallel channel outputs of the photo array. Each channel processor comprises an analog processor, an A/D converter, a First-In-First-Out ("FIFO") memory buffer and a data bus coupled to the FIFO memory buffer of each one of the channel processors. A single FIFO memory buffer is coupled to the data bus and a D/A converter is coupled to the output of the single FIFO memory buffer. The output of the D/A converter is coupled to the input of the ultrasound console. A controller coupled to an ultrasound motor encoder synchronizes the operation of the electronics interface with the ultrasound console, based on the rotation of the motor rotating the rotary connector 410 coupled to the optical fiber 407 within the catheter 408. The operation of the interface is described in more detail in the '357 application.

Where the ultrasound console is adapted to receive a digital input, the serial digital data sequence from the single FIFO memory is provided to the input of the console through control logic that controls the transfer of the digital data sequence, as is also described in the '357 application.

The photo detector array may be a multiplexed photo detector array. Electrical interfaces for single and double channel multiplexed photo detector arrays are also described in the '357 application.

Other electronic interfaces for converting the parallel output of the array of photo detectors into a serial analog or digital data stream, may also be used.

Figure 13:
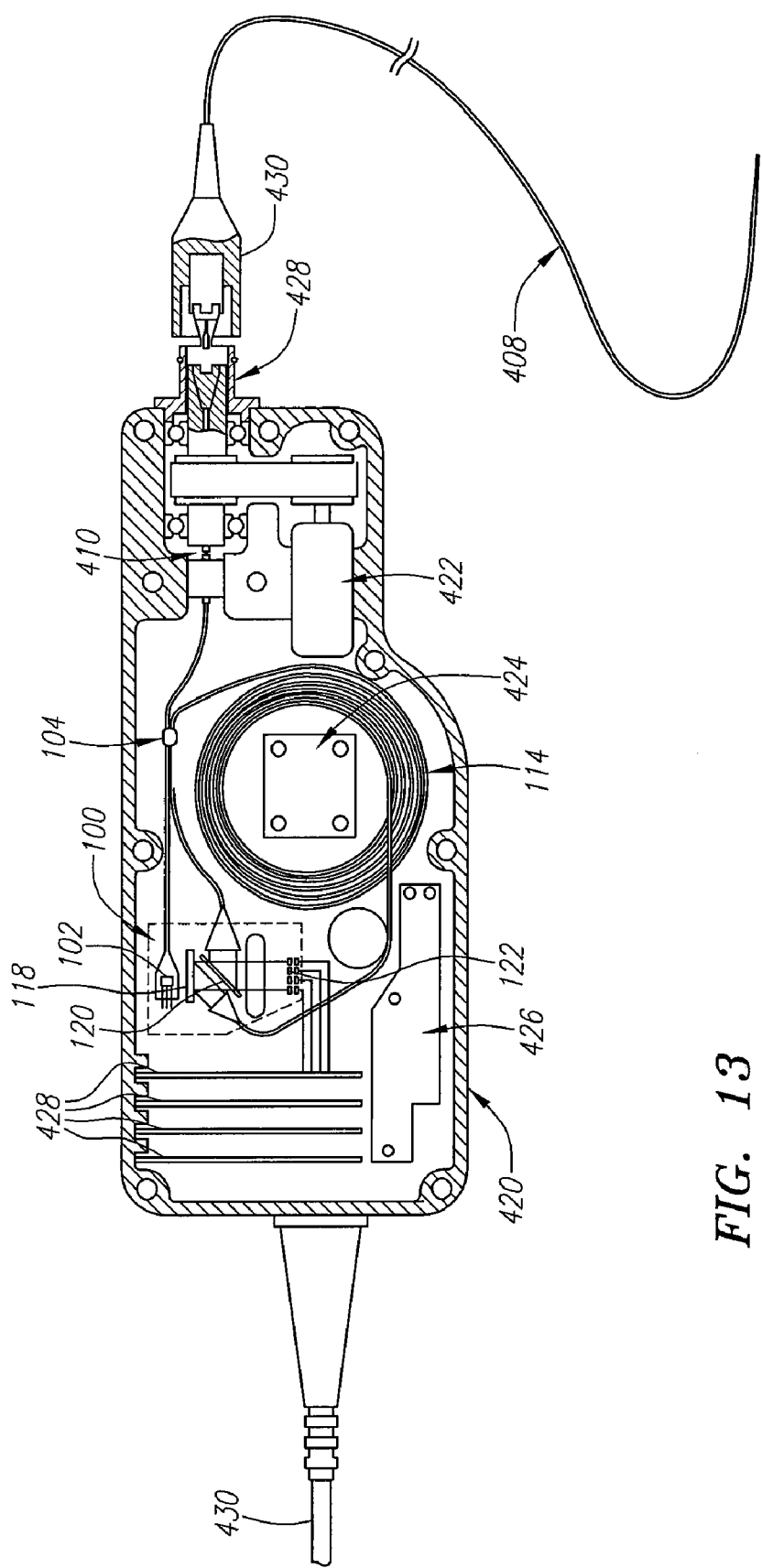
FIG. 13 shows an interferometric system in accordance with the embodiment of FIG. 3a contained within a housing for use with a interferometric catheter and an ultrasound console.

FIG. 13 shows a housing 420 containing an interferometer in accordance with the embodiment of FIG. 3a of the present invention for use with an interferometric catheter 408 and an IVUS console 396. Components common to the other embodiments are commonly numbered. The light source 102, the fiber optic beam splitter 104, the optical fibers 106, 108, 110 and 114, the diffraction grating 118, the collimators 112, 116, the open space beam splitter 120, the conjugating lens 124 and the multi-element detector 122 are shown. The rotary coupler 410 of FIG. 11 is also shown. A motor 422 is provided in the housing 420 to rotate the rotary coupler 410 and the optical fiber 407 within the catheter 408. A motor controller 424 controls the operation of the motor 422. A power supply 426 is shown, as well. Data acquisition and processing boards 428 are provided, electrically connected to a cable 430 for connection to the IVUS console 396 of FIG. 11. The parallel to serial converter 398 in FIG. 12 may be included on the processing boards. A port 428 of the housing and a catheter adapter 430 for connection to the port are shown as well.

As mentioned above, any of the embodiments of the interferometric systems described herein, as well as other fiber optic and non fiber optic OCT systems using a multi-element photo detector, may be used in the imaging system 390. For example, the systems of U.S. Pat. No. 5,943,133 and "Nonmechanical grating-generated scanning coherence microscopy", Optics Letters, Vol. 23, No. 23, Dec. 1, 1998, discussed above and incorporated by reference herein, in their entirety, may also be used.

Alternatively, an oscillating mirror or other such reflector may be used to scan a sample depth. For example, interferometers such as those described in U.S. Pat. No. 6,134,003, U.S. Pat. No. 6,111,645, U.S. Pat. No. 5,459,570, U.S. Pat. No. 5,321,501 and International Publication No. WO 98/38907 published on Sep. 11, 1998, for example, which are also incorporated by reference herein, may also be used in the imaging system with an interface disclosed in the '903 application or other such interfaces.

Another interferometric system which may be used in the imaging system 390 is described in U.S. patent application Ser. No. 09/906,903, entitled "Electronically Scanned Optical Coherence Tomography with Frequency Modulated Signals", filed on Jul. 16, 2001, assigned to the assignee of the present invention and incorporated by reference herein. There, an interferometer uses a single element detector and image depth information is carried on multiple modulation frequencies, each corresponding to a different depth. The image depth information in the signal output by the detector may be resolved by tuning to the desired frequency. Interfaces for coupling such interferometers to an IVUS console are also disclosed.

As was also mentioned above, the sample arm may be incorporated in an endoscope for insertion into the gastrointestinal tract, for example. The sample arm may also have a probe at its end for examining external biological tissue, such as the eye, or other types of samples, such as semiconductors.

While the preferred embodiments described above are implemented with fiber optics for use in examining internal biological tissue, such as biological tissue along internal body cavities and organs, the embodiments of the invention may be readily implemented with bulk optics or other optical components. For example, in examining semiconductors and external biological tissue, a non fiber optic interferometer may be used in accordance with the invention. In a non fiber optic implementation, one collimator is preferably provided between the light source and the first beam splitter.

While use of a multi-element photo detector array is preferred, a single element photo detector may also be used, in which case the width of the combined light beam could be moved across the detector or the detector could be moved across the width of the combined light beam.

Use of a focusing lens, first and second collimators and one or two conjugating lenses are also preferred, but not required.

While various embodiments of the invention have been described, it will be apparent to those of ordinary skill in the art that modifications may be made to those embodiments without going beyond the spirit and scope of the invention, as defined by the following claims and their equivalents.

We claim:

1. An interferometer comprising:

a low coherence light source;

a first beam splitter in communication with the light source, wherein the first beam splitter splits light received from the light source into a sample beam and a reference beam;

an optical circulator having a first port in communication with the first beam splitter to receive the sample beam, a second port, and a third port, wherein light input to the first port exits the optical circulator from the second port and light entering the second port exits the optical circulator from the third port;

an optical fiber in communication with the second port of the optical circulator to convey the sample beam to a sample and convey a reflected sample beam from the sample to the second port of the optical circulator;

a diffraction grating in communication with the first beam splitter to receive the reference beam, wherein the diffraction grating diffracts the reference beam into a diffracted reference beam;

a second beam splitter in communication with the diffraction grating to receive the diffracted reference beam and in communication with the third port of the optical circulator to receive the reflected sample beam, wherein the second beam splitter combines the diffracted reference beam and the reflected sample beam into a combined beam; and a detector positioned to receive the combined beam.

2. The interferometer of claim 1, further comprising analog circuitry, having parallel outputs, coupled to an output of the detector.

3. The interferometer of claim 2, further comprising a parallel to serial converter coupled to the parallel outputs of the analog circuitry, wherein the parallel to serial converter is configured to be coupled with an ultrasound console.

4. The interferometer of claim 1, wherein the optical fiber is optically coupled to a rotary connector having an output coupled with a mirror.

5. The interferometer of claim 4, wherein the optical fiber is located within a catheter.

6. The interferometer of claim 1, wherein the optical fiber is optically coupled to a rotary connector having an output coupled with a prism.

7. The interferometer of claim 1, further comprising a processor communicatively coupled with an output of the detector.

8. The interferometer of claim 1, wherein the light received from the light source has an energy and the first beam splitter splits the light into a sample light beam having more than half of the energy of the light and a reference light beam having less than half of the energy of the light.

9. The interferometer of claim 8, further comprising:
a focusing lens to focus the sample light beam onto the sample and to focus the reflected sample light beam;
a first collimator in communication with the optical circulator and the second beam splitter, wherein the first collimator collimates the reflected sample light beam and the collimated sample light beam is directed to the second beam splitter;
a second collimator optically in communication with the first beam splitter and the diffraction grating, wherein the second collimator collimates the reference light beam and the collimated reference light beam is directed onto the diffraction grating; and
a conjugating lens between the second beam splitter and the detector.

10. The interferometer of claim 1, further comprising a conjugating lens between the detector and the second beam splitter.

11. The interferometer of claim 1, wherein the detector is a multi-element photo detector.

12. The interferometer of claim 1, wherein the second beam splitter forms a second combined beam, further comprising:
a second detector positioned to receive the second combined beam; and
first and second polarization filters filter positioned to filter the first and second combined light beams, respectively with respect to first and second respective polarizations.

13. The interferometer of claim 1, wherein the second beam splitter forms a second combined beam, further comprising:
a second detector positioned to receive the second combined beam;
a second light source in communication with the first beam splitter, the second light source emitting light at a wavelength different than the wavelength of the first light source;
wherein the first detector detects light at a wavelength corresponding to the wavelength of the light emitted by the first light source and the second detector detects light at a wavelength corresponding to the wavelength of the light emitted by the second light source.

14. The interferometer of claim 13, wherein one of the light sources emits light in a wavelength band that induces fluorescence in the sample.

15. The interferometer of claim 1, wherein the second beam splitter directs more than half of the energy in the reflected sample light beam into the combined beam and less than half of the energy in the reference light beam into the combined beam.

16. The interferometer of claim 1, further comprising a phase modulator to modulate either one of the reference fight beam and the reflected sample light beam.

17. The interferometer of claim 1, wherein the diffracting grating is a reflective diffraction grating, a transparent diffraction grating, or an acousto-optic modulator.

18. The interferometer of claim 1, further comprising a catheter, wherein at least a portion of the optical fiber is within the catheter.

19. The interferometer of claim 1, further comprising:
a signal processor electrically connected to the detector to process the signals from the detector.

20. The interferometer of claim 1, wherein the light source is pulsed.

21. The interferometer of claim 1, wherein the first beam splitter splits the light received from the light source into a sample light beam having substantially more than half of the energy of the light and a reference light beam having substantially less than half of the energy of the light.

22. The interferometer of claim 1, wherein the first beam splitter directs at least about 90% of the light energy received from the light source into the sample light beam and about 10% or less of the light energy received from the light source into the reference light beam.

23. The interferometer of claim 1, wherein the first beam splitter splits the light received from the light source into a sample light beam having substantially more than half of the energy of the light and a reference light beam having substantially less than half of the energy of the light.

24. The interferometer of claim 1, wherein the second beam splitter directs at least about 90% of the light energy received from the reflected sample beam into the combined beam and about 10% or less of the light energy received from the diffracted reference beam into the combined beam.

* * * * *